(12) United States Patent
Rowe

(10) Patent No.: US 8,485,664 B2
(45) Date of Patent: Jul. 16, 2013

(54) HANDHELD REFLECTOMETER FOR MEASURING MACULAR PIGMENT

(75) Inventor: T. Scott Rowe, Dana Point, CA (US)

(73) Assignee: Ocular Prognostics, LLC, Chesterfield, MS (US)

( * ) Notice: Subject to any disclaimer, the term of this patent is extended or adjusted under 35 U.S.C. 154(b) by 0 days.

(21) Appl. No.: 13/273,050

(22) Filed: Oct. 13, 2011

(65) Prior Publication Data
US 2012/0092619 A1 Apr. 19, 2012

Related U.S. Application Data

(60) Provisional application No. 61/392,741, filed on Oct. 13, 2010.

(51) Int. Cl.
*A61B 3/10* (2006.01)
*A61B 3/00* (2006.01)

(52) U.S. Cl.
USPC .......................................... 351/221; 351/246

(58) Field of Classification Search
USPC ................................................ 351/200–246
See application file for complete search history.

(56) References Cited

U.S. PATENT DOCUMENTS

| | | |
|---|---|---|
| 4,861,154 A | 8/1989 | Sherwin et al. |
| 4,889,422 A | 12/1989 | Pavlidis |
| 5,331,969 A | 7/1994 | Silberstein |
| 6,315,412 B1 | 11/2001 | Snodderly |
| RE38,009 E | 2/2003 | Garnett et al. |
| 6,572,229 B2 | 6/2003 | Wei |
| 6,578,965 B2 | 6/2003 | Grant |
| 6,623,117 B2 | 9/2003 | Shibutani et al. |
| 6,688,744 B2 | 2/2004 | Wei et al. |
| 6,729,728 B2 | 5/2004 | Wei et al. |
| 6,834,958 B2 | 12/2004 | Cornsweet |
| 6,969,856 B1 | 11/2005 | Hillenbrand et al. |
| 7,156,518 B2 | 1/2007 | Cornsweet |
| 7,467,870 B2 | 12/2008 | van de Kraats et al. |
| 2003/0130579 A1 | 7/2003 | McClane et al. |
| 2005/0110949 A1* | 5/2005 | Goldfain et al. ............. 351/206 |
| 2007/0252950 A1* | 11/2007 | Kraats et al. ................. 351/221 |
| 2010/0097573 A1* | 4/2010 | Verdooner et al. ........... 351/206 |
| 2010/0241450 A1 | 9/2010 | Gierhart et al. |

OTHER PUBLICATIONS

PCT International Search Report for International Application No. PCT/US2011/056205 dated Feb. 22, 2012 (3 pages).

(Continued)

*Primary Examiner* — Mohammed Hasan
(74) *Attorney, Agent, or Firm* — Nixon Peabody LLP

(57) ABSTRACT

A macular pigment reflectometer is handheld, light, and portable. It can be provided as a part of a self-contained system. The self-contained system includes a docking station in which the macular pigment reflectometer is placed between uses. The docking station is used to recharge the battery of the handheld macular pigment reflectometer. The docking station also has one or more types of communication ports, such as one for a wired or wireless internet connection, through which the handheld macular pigment reflectometer can communicate with a computer or an electronic medical records system. The instrument operates in a pulsed operating mode wherein relative instrument-to-eye motion is reduced and, preferably, nearly eliminated. The handheld macular pigment reflectometer contains an on-board spectrometer which is designed to capture spectra in very short intervals of time. A trigger on the instrument allows for a rapid, intuitive, and sequential alignment followed by rapid data gathering.

22 Claims, 17 Drawing Sheets

OTHER PUBLICATIONS

PCT Written Opinion for International Application No. PCT/US2011/056205 dated Feb. 22, 2012 (6 pages).

"Effect of wavelength on in vivo images of the human cone mosaic", Stacey S. Choi, Nathan Doble, Julianna Lin, Julian Christou, David R. Williams, Journal of the Optical Society of America, vol. 22, Dec. 12, 2005 (8 pages).

"Fast and Objective Measurement of Macular Pigment With Natural Pupil" (Dirk van Norren, Jan van de Kraats, Suze Valen & Tos T.J.M. Berendschot) Apr. 30, 2005—(1-page).

"Fundus Photography for Measurement of Macular Pigment Density Distribution in Children" (Lo J. Bour, Lily Koo, Francois C. Delort, Patricia Apkarian, Anne B. Fulton) Investigative Ophthalmology & Visual Science, May 2002, vol. 43, No. 5 Copyright © Association for Research in Vision and Ophthalmology—(6-pages.).

"Comparison of Fundus Autofluorescence and Minimum—Motion Measurements of Macular Pigment Distribution Profiles Derived From Identical Retinal Areas" Anthony G. Robson, Glen Harding, Frederick W. Fitzke, Jack D. Moreland "Perception" vol. 34 2005—www.perceptionweb.com—(7-pages).

"Macular Pigment Assessment by Motion Photometry" Moreland JD.—MacKay Institute Keele University, Staffordshire, ST5 5BG, UK. j.d.moreland@cns.keele.ac.uk PubMed—Arch Biochem Biophys. Oct. 15, 2004; 430(2):143-8—(6 pages).

"Macular Pirment Optical Density Measurement: A Novel Compact Instrument" Stephen Beatty, Hui-Hiang Koh, David Carden and Ian J. Murray, Ophthal. Physical Opt. vol. 20, No. 2, pp. 105-111, 2000 © 2000 The College of Optometrists, Published by Elsevier Science Ltd. Printed in Great Britain—(7-pages).

"A Practical Method for Measuring Macular Pigment Optical Density" Billy R. Wooten, Billy R. Hammond, Jr., Richard I. Land and D. Max Snodderly Investigation Ophthalmology and Visual Science. 1999;40:2481-2489. © 1999 by The Association for Research in Vision and Ophthalmology, Inc. (14 pages).

"Macular Pigment Measurement by Heterochromatic Flicker Photometry in Order Subjects: The Carotenoids and Age-Related Eye Disease Study" D. Max Snodderly, Julie A. Mares, Billy R. Wooten, Lisa Oxton, Michael Gruber, and Tara Ficek, for the AREDS Macular Pigment Study Group Investigative Ophthalmology & Visual Science, Feb. 2004, vol. 45, No. 2 Copyright © Association for Research in Vision and Ophthalmology.—(8-pages).

"Macular Pigment" Property of the University of Westiminster, Vision Research Group John Mellerio—mellerg@wmin.ac.uk—(10 pages), Dec. 23, 2008.

"Heterochromatic Flicker Photometry" Department of Physics. Florida International University, Miami 33199, USA Bone RA, Landrum JT.—bone@fiu.edu PubMed—Arch Biochem Biophys, Oct. 15, 2004;430(2):137-42—(6 pages.)

"A Portable Instrument for Measuring Macular Pigment With Central Fixation" Mellerio J, Ahmadi-Lari S, van Kuijk F, Pauleikhoff D, Bird A, Marshall J. (11 pages).

"Macular Pigment Density Measured by Autofluorescence Spectrometry: Comparison with Reflectometry and Heterochromatic Flicker Photometry" Delori FC, Goger DG, Hammond BR, Snodderly DM, Burns SA. Schepens Eye Research Institute, Boston, Massachusetts 02114, USA. PubMed—Opt Soc Am A Opt Image Sci Vis. Jun. 2001;18(6):1212-30.—(19 pages).

"Autofluorescence Method to Measure Macular Pigment Optical Densities Fluorometry and Autofluorescence Imaging" Francois C. Delori Schepens Eye Research Institute and Harvard Medical School, Boston, M.A. USA © 2004 Published by Elsevier Inc.—(7 pages).

"Resonance Raman Measurement of Macular Carotenoids in the Living Human Eye" Paul S. Bernstein, Da-You Zhao, Mohsen Sharifzadeh, Igor V. Ermakov, Werner Gellermann Department of Ophthalmology and Visual Sciences, Moran Eye Center Univeristy of Utah School of Medicine, Salt Lake City, UT, USA, Department of Physics, University of Utah, Salt Lake City, UT © 2004 Elsevier Inc.—(7 pages).

"Influence of Lutein Supplementation on Macular Pigment, Assessed with Two Objective Techniques" Tos T. J. M. Berendschot[1], R. Alexandra Goldbohm [2], Wilhelmina A.A. Klöpping [2], Jan van de Kraats[1], Jeannette van Norel [1], and Dirk van Norren [1] © 2000 by The Association for Research in Vision and Ophthalmology, Inc.—(1 page).

"Influence of Lutein Supplementation on Macular Pigment, Assessed With Two Objective Techniques" Berendschot TT, Goldbohm RA, Klopping WA, van de Kraats J, van Norel J, van Norren D. University Medical Centre Utrecht, Department of Ophthalmology, The Netherlands PubMed—Invest Ophthal. Vis. Sci. Oct. 2000; 41(11):3322-6.—(5 pages).

"Objective Determination of The Macular Pigment Optical Density Using Fundus Reflectance Spectroscopy" Tos T.J.M. Berendschot and * Dirk van Norren department of Opthalmology, University of Medical Center Utrecht, The Netherlands © 2004 Elsevier, Inc.—(7-pages).

"Current Concepts in the Pathogenesis of Age-Related Macular Degeneration" Marco A. Zarbin, MD, PhD. Arch Ophthalmol./vol. 122. Apr. 2004—www.archophthalmol.com © 2004 American Medical Association.—(17 pages).

"Assessment of the Validity of in Vivo Methods of Measuring Human Macular Pigment Optical Density" Hammond BR Jr., Wooten BR, Smollon B. Vision Science Laboratory, University of Georgia, Athens, Georgia 30602-3013, USA PubMed—Optom Vis. Sci. May 2005; 82(5):387-404—(17 pages).

InVivo Assessment of Retinal Carotenoids: Macular Pigment Detection Techniques and Their Impact On Monitoring Pigment Status Joanne Curran Celentano, Joanne D. Nurke and Billy R Hammond, Jr Department of Psychology and Behavior Sciences, University of Georgia, Athens, GA © 2002 American Society for Nutritional Sciences—(5 pages).

"Macular Degeneration—The Latest Scientific Discoveries and Treatments for Preserving Your Sight" Robert D'Amato, M.D., Ph.D., and John Snyder Copyright © 2000 by Robert d'Amato and Joan Snyder—(2 pages).

"Age-Related Macular Degeneration" Jeffrey W. Berger, Stuart L. Fine and Maureen G. Maguire, Mosby, 1999.Jul. 2002 / 576 pp, illus. /ISBN: 08247-0682-X—(3-pages).

"The pathways of light measured in fundus reflectometry," J. van. de. Kraats, T.T.J.M. Berendschot, and D.van Norren, 1996, Vision Res. 36 (19 pages).

"Spectral reflectance of the human ocular fundus," F.C. Delori and K.P. Pfibsen, 1989, Appl. Opt. 28 (18 pages).

"Visible and near infrared light absorption in pigment epithelium and choriod," V.P. Gabel, R. Birngruber, and F. Hillenkamp, *Excerpta Medica, International Congress Series* No. 450, K. Shimizu and J.A. Oosterhuis, eds, (Elsevier, Amsterdam, 1978) (4 pages).

"Biological control of primate macular pigment. Biochemical and densitometric studies," G.J. Handelman, D.M. Snodderly, N.I. Krinsky, M.D. Russett, and A.J. Alder, Invest. Ophthalmol. 1991, Vis. Sci. 32 (11 pages).

"Aging of the human lens," J. Pokorny, V.C. Smith, and M. Lutze, Appl., Opt. 26, 1987 (4 pages).

O.W. van Assendelft, *Spectroscopy of hemoglobin derivatives*, C.C. Thomas ed., (C.C. Thomas, Springfield, IL, 1979) (2 pages).

"Spectral reflectance of the human eye," D. van Norren and L. F. Tiemeijer, Vision Res. 1986, 26 (8 pages).

"Lutein and Zeaxanthin Measured Separately in the Living Human Retina with Fundus Reflectometry," Jan van de Kraats. Martijn J. Kanis, Stijn W. Genders, Dirk van Norren, Investigative Ophthalmology & Visual Science, vol. 49, No. 12, Dec. 2008 (6 pages).

* cited by examiner

HANDHELD REFLECTOMETER FOR MEASURING MACULAR PIGMENT

CROSS REFERENCE TO RELATED APPLICATION

This application claims the benefit of priority of U.S. Provisional Application No. 61/392,741, filed Oct. 13, 2010, which is hereby incorporated by reference in its entirety.

FIELD OF INVENTION

The present invention relates to a handheld macular pigment reflectometry instrument that measures characteristics of the patient's eye, such as macular pigment, with a high degree of accuracy and without dilating the patient's pupil. The invention also relates to a way to align an instrument to a point or region within a patient's eye that allows for a rapid, intuitive and sequential alignment procedure and for rapid data gathering once alignment is achieved.

BACKGROUND OF THE INVENTION

The Retina and Retinal Diseases: The retina is the layer of nerve cells at the back of the eye, which convert light into nerve signals that are sent to the brain. In humans, and in other primates (but not in most other mammals, or other types of animals), the retina has a small yellowish area in the center of the field of vision. That yellowish area is called the "macula." It provides fine resolution vision in the center of the visual field and is essential to good vision. People who suffer from macular degeneration often lose the ability to read, recognize faces, drive, or walk safely on unfamiliar routes.

The surrounding portions of the macula can only provide coarse resolution. This physiological feature limits and controls the number of nerve signals that the brain must rapidly process, to form coherent rapid-response vision, and it also helps limit and control the huge number of rod and cone receptors that the eye must continually regenerate and recycle, every day. Many people do not realize the retina can provide only coarse resolution, outside of a limited central area, because the eyes and the brain have developed an extraordinary ability to synthesize coherent vision from a combination of fine and coarse resolution. During that type of vision synthesis, the eye muscles cause the eyes to flit back and forth over a larger field of vision, pausing at each location for just an instant while the eye quickly "grabs" a fine-resolution image of a limited area. This process occurs so rapidly that a person does not notice it happening, and does not pay attention to how a complete visual image and impression is being assembled and updated from combinations of fine and coarse resolution images.

There is also a peculiar anatomic structure in the retinas of humans, which points out the difference between fine resolution (provided by the macula) and coarse resolution (provided by the remainder of the retina). In humans, the blood vessels that serve the retina actually sit in front of the retina, where they can block and interfere with incoming light, before the light reaches the retina. This is counter-intuitive, and one should wonder why the retina evolved with a physical handicap that literally gets in the way of good, clear vision. The answer is, in those parts of the retina, only coarse vision is being created, and blood vessels positioned in front of the retina do not interfere with that type of coarse vision. By contrast, in the macular region in the center of the retina, the blood vessels in front of the retina are lacking and supply is only from blood vessels present anywhere behind the layer of neurons with rod and cone receptors. This is consistent with the macula providing fine resolution vision, which would be blocked and hindered if the blood vessels were located in front of the neurons, in ways that would intercept and blocking portions of the incoming light.

"Retinal degeneration" is a descriptive term, which refers to and includes an entire class of eye diseases and disorders. It includes any progressive disorder or disease that causes the macula to gradually degenerate, to a point that substantially impairs or damages eyesight and vision. Several major categories of retinal degeneration are known. These include: (i) age-related macular degeneration, which gradually appears among some people over the age of about 65; (ii) diabetic retinopathy, in which problems with sugar and energy metabolism damage the entire retina, including the macula; (iii) eye diseases that affect the macula due to gene and/or enzyme defects, such as Stargardt's disease, Best's disease, Batten's disease, Sjogren-Larsson syndrome, and various other eye disorders that lead to gradual degeneration of the macula (and possibly other parts of the retina) over a span of time. This is not an exclusive list, and other subclasses and categories also are known. For example, age-related macular degeneration is subdivided into wet and dry forms, depending on whether abnormal and disruptive blood vessel growth is occurring in the structural layers behind the retina.

The causes and effects of macular degeneration, and efforts to prevent or treat it, are described in numerous books (e.g., "Macular Degeneration," by Robert D'Amato et al (2000) and "Age-Related Macular Degeneration," by Jennifer Lim (2002)), articles ("Age-Related Macular Degeneration" by Berger et al (1999)) and patents, such as U.S. Pat. No. Re. 38,009, which is assigned to ZeaVision LLC, and is incorporated by reference in its entirety.

In recent years, awareness has grown, among some researchers but not among the general public, of the roles that macular pigment plays, in the health and longevity of the macula. Therefore, the two carotenoid pigments that create and provide the macular pigment are discussed below.

The Macular Pigments: Zeaxanthin and Lutein: The macula has a yellowish color because it contains unusually high concentrations of two specific pigments, called zeaxanthin and lutein. Both are carotenoids, similar to beta-carotene but with hydroxyl groups coupled to their end rings (the presence of one or more oxygen atoms causes a carotenoid to be categorized as a "xanthophyll", so zeaxanthin and lutein are sometimes referred to as xanthophylls). Both of those two carotenoids are known to be protective and beneficial, in human retinas, by mechanisms that include: (1) absorption of destructive ultraviolet photons; and (2) quenching of destructive radicals. Both of those mechanisms, and other potential protective mechanisms, are discussed below.

In addition to their involvement in the macula and macular degeneration, zeaxanthin and lutein also are present in other eye structures (including the eye lens), and undesirably low levels of those two carotenoids appear to be correlated with higher risks of disorders such as cataracts. Accordingly, although the discussion herein focuses on macular degeneration, it should be recognized that any comments herein about macular pigment levels also have varying degrees of relevance to some other eye disorders as well. Similarly, any comments herein about macular degeneration should be recognized as including disorders that are referred to by other names (such as diabetic retinopathy, Stargardt's disease, etc.), but that involve or lead to gradual deterioration of the macula.

The structures of zeaxanthin and lutein are very similar because they are isomers of each other, differing only in the placement of a double bond in one end ring. In lutein, the ring with a "misplaced" double bond is called an "epsilon" ring. All of the other end rings have "beta" ring structures, which refer to the sequence of double bonds found in beta carotene's two end rings.

However, that single minor structural difference, between zeaxanthin versus lutein, has profound effects on the traits, performance, and tissue concentrations of those two different molecules, in both plants and animals. Briefly, the lutein molecule has a bend where the epsilon ring joins the "straight chain" segment between the two end rings. That bend, near one end, allows lutein to fit properly into ring-shaped "light-harvesting" structures, in the chloroplasts of plant cells. Since light-harvesting (which is part of photosynthesis) is crucial in plants, lutein evolved as a major and dominant carotenoid, in essentially all plants.

By contrast, zeaxanthin does not have a bend at either end. Since it is relatively straight, it cannot fit properly into the circular light-harvesting structures that help carry out photosynthesis, in plants. Therefore, it evolved in plants in ways that led to a very different role in a day-night cycle, in which zeaxanthin and a similar carotenoid called violaxanthin are converted back and forth into each other. As a result, zeaxanthin does not accumulate in substantial quantities in most types of plants (although a few exceptions are known, such as corn and red peppers). Even in dark green plants, such as spinach or kale, lutein content is dozens or even hundreds of times greater than zeaxanthin content. On an aggregate basis, the total amount of zeaxanthin in typical diets in industrial nations is believed to be about 1% (or possibly even less) of the total lutein supply.

Another important difference between zeaxanthin and lutein is that zeaxanthin has a longer and more protective "conjugated cloud" of electrons surrounding it, compared to lutein. When a series of carbon atoms are bonded to each other by alternating double and single bonds, the electrons become mobile, and are no longer affixed to specific bond locations. Those electrons form a flexible and movable electron "cloud". This same type of cloud also appears in benzene rings and other "aromatic" organic compounds, and it is well-known to chemists.

That type of flexible and movable electron cloud is ideally suited for absorbing high-energy radiation (in the ultraviolet, near-ultraviolet, and deep blue part of the spectrum), without suffering damage or breakage of the molecule. In addition, a flexible and movable electron cloud is ideally suited for neutralizing and "quenching" oxygen radicals, which are aggressively unstable and destructive molecules, containing oxygen atoms having unpaired electrons. Oxidative radicals are important damaging agents in any cells and tissues that are being bombarded by high levels of UV radiation, since UV radiation often breaks bonds that involve oxygen atoms, in ways that create unpaired electrons where the broken bonds previously existed.

All carotenoids are assembled, in plants, from a 5-carbon precursor called isoprene, which has two double bonds separated by a single bond. As a result, all carotenoids have at least some sequence of alternating double and single bonds, leading to a conjugated electron cloud covering at least part of the carotenoid molecule. This is a basic and shared trait of all carotenoids, and it explains how carotenoids provide two crucial benefits (i.e., absorption of UV radiation, and quenching of destructive radicals) that are vital to plants, which must often sit in direct sunlight for hours each day.

However, different carotenoids have conjugated electron clouds that different lengths, and different potencies and protective traits. In particular, there is a crucial difference between the conjugated electron clouds of zeaxanthin and lutein. The placement of the double bonds in both of zeaxanthin's two end rings continues and extends the pattern of alternating double and single bonds, from the straight chain. This extends zeaxanthin's conjugated and protective electron cloud, out over a part of both of zeaxanthin's two end rings.

By contrast, the position of the double bond in lutein's "epsilon" ring disrupts the alternating double/single bond sequence, established by the straight-chain portion of the molecule. This disrupts and terminates the conjugated electron cloud, and it prevents the protective, UV-absorbing, radical-quenching electron cloud from covering any part of lutein's epsilon end ring. That structural difference in their end rings becomes highly important, because zeaxanthin and lutein are deposited into animal cells in ways that cause them to "span" or "straddle" the outer membranes of the cells. It causes zeaxanthin and lutein to be deposited into animal cell membranes in a way that places them perpendicular to the surfaces of the membrane that surrounds and encloses a cell.

It is not fully known, at a molecular level, how lutein's lack of symmetry, and lack of a protective conjugated electron cloud over one end ring, affect its deposition in cells in the human macula. For example, it is not known whether the protective beta rings at one end of lutein are consistently or predominantly placed on either the external or internal surfaces of cell membranes. In addition, it is not known whether lutein is consistently deposited, into human cell membranes, in a membrane-spanning orientation.

However, other aspects of zeaxanthin and lutein content and deposition in blood, and in the macular regions of human retinas, are well-known. Despite the rarity of zeaxanthin in food sources (as mentioned above, zeaxanthin content in typical diets is believed to be less than about 1% of the lutein supply), zeaxanthin concentrations in human blood average about 20% of lutein levels. This clearly indicates that the human body does something that indicates a selective preference for zeaxanthin, over lutein.

Even more revealingly, zeaxanthin is even more concentrated in the crucially important center of the human macula, which provides fine-resolution vision in humans. In the crucially important center of a healthy human macula, zeaxanthin is present at levels that average more than twice the concentrations of lutein. By contrast, lutein is present in higher levels around the less-important periphery of the macula. While the mechanisms which create that pattern of deposition are not fully understood, it recently has been reported that certain enzymes that appear to be involved will clearly bind to zeaxanthin with relatively high affinity under in vitro conditions; however, those same enzymes will not bind to lutein with any substantial affinity (Bhosale et al 2004).

Accordingly, these differences in how zeaxanthin and lutein are deposited in the macula provide strong evidence that the macula wants and needs zeaxanthin, more than lutein. The patterns of deposition, and the known structural and electron cloud differences, suggest and indicate that the macula wants and needs zeaxanthin, and it uses lutein only if and when it cannot get enough zeaxanthin.

This belief is also supported by another important finding. The macula may attempt to convert lutein into zeaxanthin. However, the conversion process cannot convert lutein into the normal stereoisomer of zeaxanthin found in plants and in the diet (the 3R,3'R stereoisomer). Instead, it converts lutein into a different stereoisomer that has never been found in any food sources or mammalian blood. That non-dietary isomer has one end ring with the conventional "R" configuration; however, the second end ring has an unnatural "S" configuration that is never found in the normal diet. That S-R isomer (and R-S isomer) is called meso-zeaxanthin.

Consequently, while lutein may have benefits, a growing body of knowledge and evidence indicates that zeaxanthin is the ideal carotenoid for helping prevent and treat the class of eye diseases that fall into the category of retinal degeneration.

Measuring Macular Pigment: One method of measuring a patient's macular pigment is objective fundus reflectometry or densitometry. This method involves illuminating the retina with a known spectral signature illuminant and collecting and measuring the spectral return light with a variety of detectors. The returned spectral signature, or the luminance as a function of wavelength, can be used to deduce much about a patient's eye health. One use has been to measure the macular pigments in the immediate surrounds of the fovea centralis. It is these pigments that may give an indication of the level of natural protection given to the cones against harmful blue light. In particular, zeaxanthin and lutein are responsible for much of the absorption of the macular pigment. In many macular pigment density measurement schemes, these are measured collective and reported as macular pigment optical density.

U.S. Pat. No. 7,467,870 discloses a macular pigment reflectometer that can measure and report the optical density contributions of zeaxanthin and lutein separately. The macular pigment reflectometer disclosed in the '870 patent is typically a table-mounted instrument that may permit a patient to self-align the instrument for accurate measurement. Once alignment is achieved, the operator of the macular pigment reflectometer conducts the data collection process.

It has generally been challenging to align precision ophthalmic instruments to the human eye. It has been particularly challenging to align an instrument in order to visualize one particular feature of the eye such as the fovea. Handheld instruments are even more difficult to align because the patient, clinician and instrument are in simultaneous asynchronous motion. For alignment, light must get from the instrument, through the eye, to the pupil, and on through the posterior chamber to the retina and back out to the instrument and on to a detector of some nature.

Examples of ophthalmic instruments that have been traditionally difficult to align include ophthalmic fundus cameras such as the Nidek AFC 230/210 fundus camera, macular pigment reflect meters, and optical coherence tomographers. Instrument designers of these instruments have attempted to solve alignment challenges in a number of ways. This includes changing the field of view and working distance in order to present both an anterior and posterior field of view to a detector. This involves interchanging a group of optics to provide for the two fields of view which could be switched at will. One drawback to this approach is that the instrument is large and bulky because two groups of optics are required. Another drawback is the cost of these instruments and that the transition time is a function of how fast the instrument or operator can move and then stabilize these groups of optics.

Another approach has been to design the instrument with two simultaneous viewing channels in which either or both viewing channel could be coupled to one or more imaging detectors. This approach eliminates the transition time issue present in the moving optics approach. However, this approach is problematic because the optics are not arranged in a spatially efficient approach, resulting in a bulky instrument that is difficult to operate. Neither this approach nor the previously described approach is well suited to the needs of a handheld instrument in which bulk, speed, and ease of use are important.

The present invention overcomes these problems by providing a handheld macular pigment reflectometer that is a self-contained system, reduces the errors associated with the motion of typical handheld devices, can operate in dark or illuminated rooms, and includes an enhanced alignment feature.

SUMMARY OF THE INVENTION

According to one aspect of the invention, a macular pigment reflectometer is provided that is handheld. This handheld macular pigment reflectometer is light and portable.

According to another aspect of the invention, a handheld macular pigment reflectometer is provided that is a part of a self-contained system. The self-contained system includes a docking station in which the macular pigment reflectometer is placed between uses. The docking station is used to recharge the battery of the handheld macular pigment reflectometer. The docking station also has one or more types of communication ports, such as one for a wired or wireless internet connection, through which the handheld macular pigment reflectometer can communicate with a computer or an electronic medical records system.

According to another aspect of the invention, a handheld macular pigment reflectometer is provided that operates in a pulsed operating mode wherein relative instrument-to-eye motion is reduced and, preferably, nearly eliminated. The handheld macular pigment reflectometer contains an on-board spectrometer which is designed to capture spectra in very short intervals of time. Thus, there is less relative motion during spectral capture and the instrument is more likely to be aimed at the fovea during capture. The instrument employs software algorithms that will analyze each captured spectra to see if it matches an expected fovea spectra, and will flag the user if the spectral signature appears to be suspect, i.e. from outside the foveal region or simply too low in signal. The instrument preferably captures a minimum of 5 spectra during each measurement, and after auto sorting and analysis, will average the acceptable spectra. Different spectral noise reduction techniques may be used, such as boxcar averaging.

According to another aspect of the invention, a handheld macular pigment reflectometer is provided that utilizes light emitting diode (LED) technology for its light source. The LED technology significantly shortens the period of time needed to achieve lamp source stability, allowing the light source to be operational nearly instantaneously. The LED technology will likely eliminate the need to perform dark calibration checks for each macular pigment measurement performed by the handheld macular pigment reflectometer.

According to another aspect of the invention, a hand-held macular pigment reflectometer is provided that utilizes a plurality of LEDs that make up the posterior light source (LED light engine). This plurality of LEDs are combined together to emit a very broad spectrum of visible to near-infrared light, namely 400 to 880 nm. Typically, five or more LEDs can be combined to create such a light engine, although more or less may be used.

According to another aspect of the invention, a handheld macular pigment reflectometer is provided that can be used in an illuminated exam room. The handheld macular pigment reflectometer contains an eye-cup light seal. The eye cup fits to the patient's facial orbital structure, blocking most of the light from the illuminated room. In a preferred embodiment, any light from the room that gets through to the spectrometer is measured as background noise and subtracted.

According to another aspect, the present invention includes a three-step method of aligning an ophthalmic instrument to a point or region within an eye. This method of alignment allows for a rapid, intuitive, and sequential alignment followed by rapid data gathering. During the three-step alignment, the anterior image alignment takes advantage of a specular reflection from the cornea of the LED ring light source. This reflection forms a bright, sharply defined ring image at the CCD as a result of specular reflection from the anterior surface of the cornea, and can also be used to establish both instrument lateral positions (X,Y) with respect to the pupil, and also angular location with respect to the optical/visual axis of the eye. With both indications, it is much more likely that when the switch is made to the narrow retinal field of view, the image will be located on the visual axis and, thus, on or near the fovea (i.e., the target tissue of interest in the macular pigment reflectometer).

The retinal image is initiated by squeezing a trigger switch on the image from the first position to the second position. The second position shuts down the anterior LEDs and CCD, engages the posterior LEDs ("engine") and posterior CCD. A first anterior flip minor moves to the "OUT" position, the Common path objective lens optics correct for refractive error, and the posterior image is displayed. The subject eye fixates on the posterior LED light source. The measurement is taken when the trigger switch is squeezed to the third position. The screen freezes, the green reticule on the screen turns red, a second flip minor engages to the "IN" position, and all light is directed to the spectrometer through a fiber optic. The spectrometer takes five readings in 0.25 seconds, calculates an average, and then the second flip minor is returned to the "OUT" position. If the trigger is held down for more than 1 second, the red reticule flashes. The optical densities are calculated once the trigger is fully released. Position "0" is then the non-engaged, fully released position.

The invention provides an ophthalmic instrument that employs a method of using the disclosed alignment invention. This instrument is designed to provide for two partially coincident optical paths, an initial anterior optical path, and an interior following posterior optical path. The anterior optical path is designed to facilitate alignment, both from an illumination and imaging function. This optical path typically leaves a central obscuration at the image plane. This obscuration can be created optically by masks, or electronically within the CCD readout/display function. In this invention, the obscuration is not detrimental to the function of the anterior image and can be used to facilitate alignment for rapid transition to the posterior image. The obscuration is only visible in the anterior mode.

According to yet another aspect of the invention, an ophthalmic instrument is provided that employs the disclosed alignment invention and in which, with the exception of the two Common path objective lens groups, each optical path is separate from the other. The anterior first flip in-out mirror sequentially engages the two paths, redirecting the anterior path and moving out of the way to allow for the posterior path.

The invention also provides an ophthalmic instrument in which each optical path has its own imaging detector. This way, each detector can be optimized for its use. Earlier systems that had two fields of view were designed such that they used only one detector.

According to a further embodiment, a reflectometry instrument to measure macular pigment of a macula of a human eye comprises a housing including a lower hand-held portion and an assembly of optical elements arranged within the housing to sequentially image the eye with multiple fields of view and to illuminate the eye with multiple light sources. The instrument also includes an actuatable trigger switch having a first trigger switch position, a second trigger switch position and a third trigger switch position. The instrument further includes a spectrally-modifiable light source for emitting an illumination beam in a direction toward the macula. The spectrally-modifiable light source provides a range of spectra depending on the position of the actuatable trigger. The instrument further includes a spectrometer for measuring one or more spectra measurements of a detection beam. The detection beam is reflected from the macula, and each of the one or more spectra measurements is indicative of the amount of the macular pigment in the macula. The spectrometer further combines the one or more spectra measurements to result in a macular pigment optical density measurement.

According to another embodiment, a hand-held reflectometry instrument to measure macular pigment of a macula of a human eye comprises a housing including an actuatable trigger switch having a first switch position, a second switch position and a third switch position. The instrument further includes a first light source within the housing for emitting an illumination beam in a direction toward the macula and a spectrometer within the housing for measuring a detection beam. The detection beam is a portion of the illumination beam reflected from the macula, and is indicative of the amount of the macular pigment in the macula.

According to yet another embodiment, a method of determining an amount of macular pigment in the macula of a human eye comprises the acts of using a multi-step alignment process involving (i) a first light source to provide an alignment relative to a patient's pupil, and (ii) a second light source to provide alignment relative to the patient's retina after alignment relative to the patient's pupil. The method also includes, after the alignment process, (iii) activating a measurement process by passing an illumination beam through a lens system and onto the macula. The method further includes receiving, with a spectrometer, a detection beam reflected from the macula, and measuring characteristics of the detection beam at the spectrometer.

Additional aspects of the invention will be apparent to those of ordinary skill in the art in view of the detailed description of various embodiments, which is made with reference to the drawings, a brief description of which is provided below.

DETAILED DESCRIPTION

Figure 1:
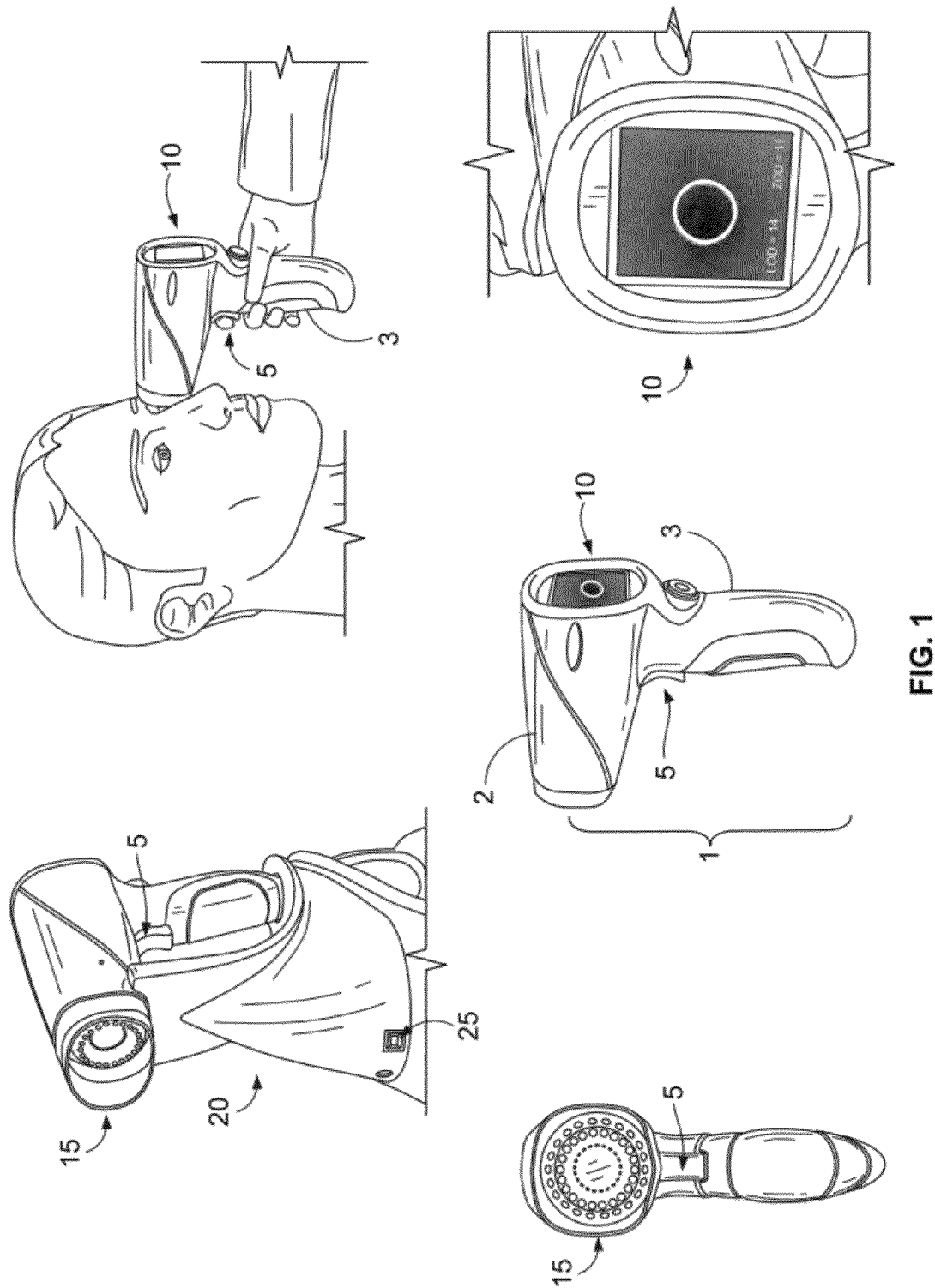
FIG. 1 is an illustration the handheld macular pigment reflectometer from a variety of views.

FIG. 1 illustrates a handheld macular pigment reflectometry (MPR) instrument 1 adapted for clinical use. The handheld MPR instrument 1 includes a housing 2 having a lower portion 3 that is ergonomically shaped to be received by an operator's hand. The handheld MPR instrument 1 enables clinician alignment and operation through a simple trigger switch 5 on the lower portion 3 actuated by a three-step alignment process that corresponds to a first trigger switch position (FIG. 5a), a second trigger switch position (FIG. 6a), and a third trigger switch position (FIG. 7a), which are discussed below.

The handheld MPR instrument 1 includes a display 10 that enables the clinician to check alignment process and view zeaxanthin and lutein optical density readings as well as the status of any diagnostic functions of the handheld MPR instrument 1. The handheld MPR instrument 1 includes an eye cup or eye shield 15, which allows the clinician to use the device in an illuminated room. The handheld MPR instrument 1 can be coupled to a base docking station 20, which can be used to charge a battery 22 located within the handheld MPR instrument 1. The battery 22 provides power to various components in the handheld MPR instrument 1 through drive circuitry 24. More details of this self-contained system are discussed below with respect to FIG. 3.

Figure 2A:
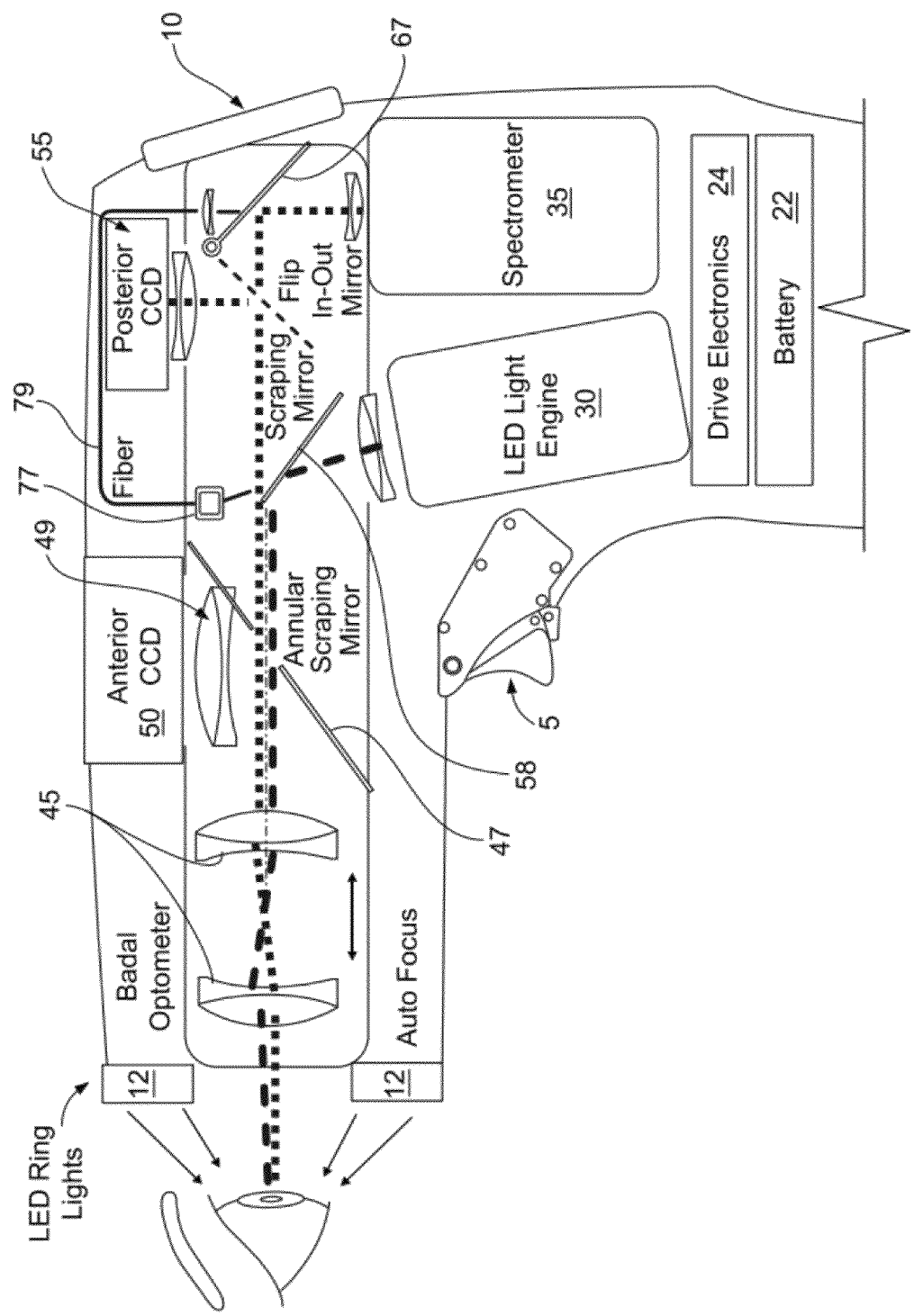
FIG. 2a is an illustration of the internal architecture of a handheld macular pigment reflectometer, according to one embodiment.

FIG. 2a illustrates the internal architecture of the handheld MPR instrument 1, according to one embodiment. The handheld MPR instrument 1 contains a first light source 12 that is preferably arrayed in a ring within the eye cup or eye shield 15 and preferably utilizes LED illumination. The first light source 12 creates a specular reflection from the cornea that is used in the alignment process (described in more detail below with reference to FIG. 5a). Light reflected from the anterior portion of the eye is captured, focused and relayed by a Badal Optometer 45 back to the annular scraping mirror 47. The Badal Optometer 45 consists of two lenses (the front two lenses in FIG. 2a), with at least one of them being moveable relative to the other one as indicated by the double-arrowed line below the Badal Optometer 45. In a preferred embodiment, the posterior lens is moveable via a small motor. This annular scraping minor 47 eliminates a central circular portion (e.g. 4 mm diameter) of the image, and relays the now annular image through a focusing lens 49 to the anterior charge coupled device (CCD) imager 50. The images captured by this CCD imager 50 are displayed on screen 10 and used for initial alignment of the handheld MPR instrument 1.

As the trigger 5 is further pulled to its second position (described in more detail in FIG. 6a), the ring LED 12 is shut down, and a second light source (or light engine) 30 is initiated. This light engine 30 is preferably a combination of a plurality of LEDs (e.g. five LEDs) that, when spectrally combined, provide a spectral range from 400 nm to 880 nm. Once the individual LEDs are ramped to their steady state position, the light from the light engine 30 is collimated, strikes a scraping minor 58 that reflects the majority of the light, but passes about 15% of the light. The reflected light passes through the annular scraping minor 47, through the Badal optometer 45 (which now acts as refractive error correction optic), and on to the patient.

The light from the light engine 30 passes through the patient's cornea and lens, reflects off of the retina and returns back through the eye's optics to the handheld MPR instrument 1. The area illuminated on the retina is about 1.0 mm in diameter, which is approximately 4 degrees of an arc. In particular the reflectance curve from this region of the retina will show the contributing factors of absorption of the carotenoids, lutein and zeaxanthin. The reflectance and absorption of the light in the eye is described in more detail (e.g. FIGS. 5a and 5b, and accompanying specification) in U.S. Pat. No. 7,467,870, which is herein incorporated by reference in its entirety.

Light returning to the handheld MPR instrument 1 now passes back through the same optics from which it came, except that the returning light will now largely miss both scraping minors 47 and 58, but will strike the flip-in minor 67 in its "IN" position, and reflect upwardly to the posterior CCD imager 55. In response to the reflected energy being received by the CCD imager 55, a 4-degree image of the macula is formed and displayed on the screen 10. Further alignment by the clinician may be anticipated, but getting the pupil aligned first significantly eases the alignment task.

Meanwhile, while the eye is being aligned, the light from the light engine 30 (15% of the output from the light engine 30) that is not reflected by the scraping mirror 58 passes on to a collection optic 77 and into a fiber 79, which re-directs it to the spectrometer 35. This light is checked by the spectrometer 35, and sets the "white balance" or native spectral signature for the light source 30 for the spectrometer 35.

Figure 7A:
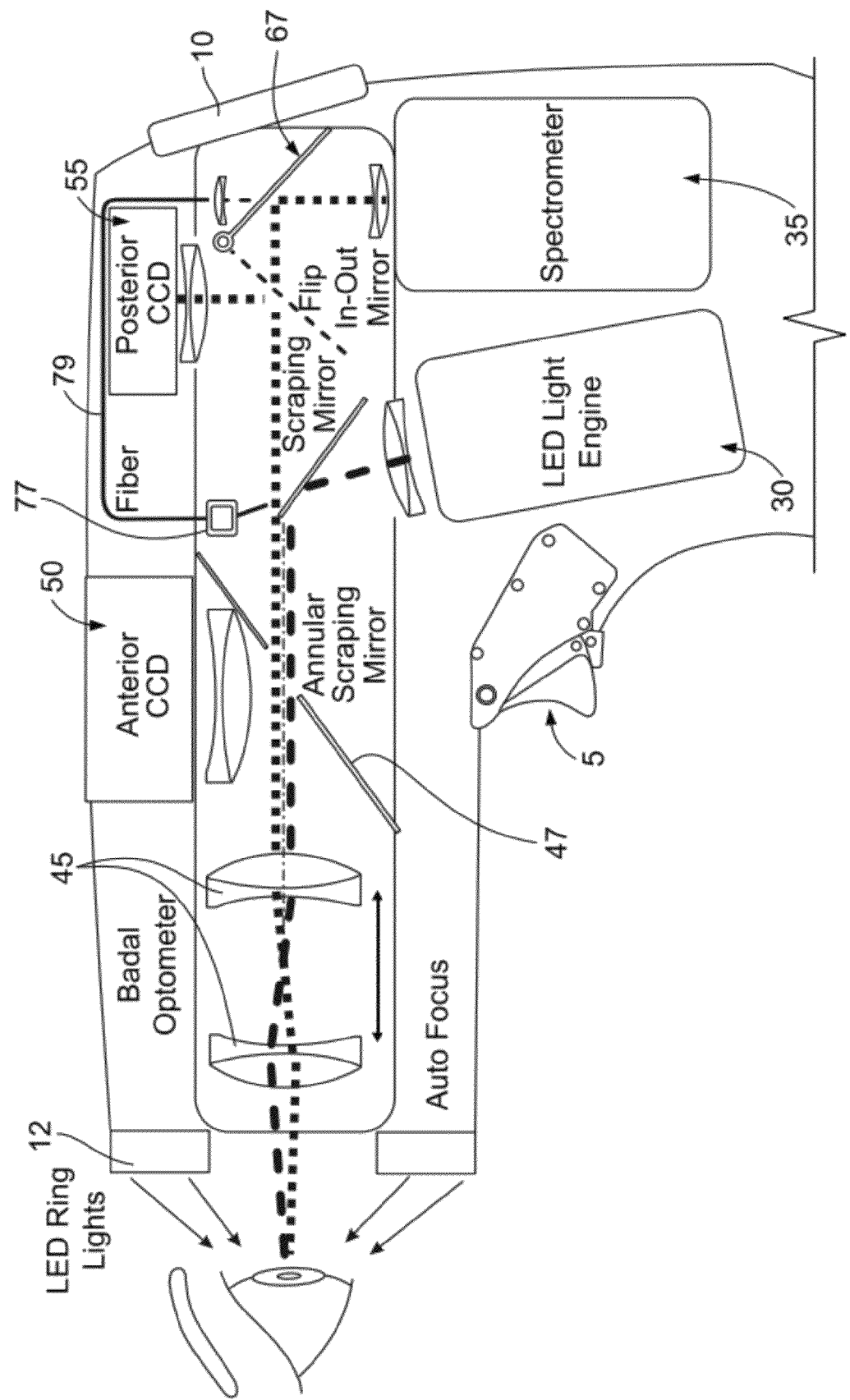
FIG. 7a is an illustration of the third position of the trigger switched actuated alignment, according to one embodiment.

Once the eye is aligned and in focus, the trigger switch 5 is pulled to its third and final position (described in more detail in FIG. 7a). The light engine 30 ramps up to its "flash" condition, which is a pulse of energy such as a 250 millisecond pulse of light that will be approximately three times the brightness as the steady-state condition when the trigger 5 is in the second position. As this occurs, the flip-in minor 67 moves to the "OUT" position, which will block the "white-balance" light from the fiber 79, but will allow for all light that normally would be incident upon the posterior CCD 55 to now enter the spectrometer 35 (possibly through some collection optics, including a short fiber).

The spectrometer 35 will take a plurality of spectral readings, such as five sequential spectra that are 50 milliseconds each, during the 250 millisecond flash. The spectrometer 35 sorts the spectra for a variety of reject criteria, and of the spectra it keeps, will average them and calculate the lutein optical density (LOD), the zeaxanthin optical density (ZOD), and the combined macular pigment optical density (MPOD). The numbers will displayed on display 10 to the clinician, and saved in memory in a microcomputer system (not shown). The clinician releases the trigger 5 and can repeat the procedure, as necessary. The detail of analysis that determines these density values is set forth in U.S. Pat. No. 7,467,870, which is herein incorporated by reference in its entirety.

Figure 3:
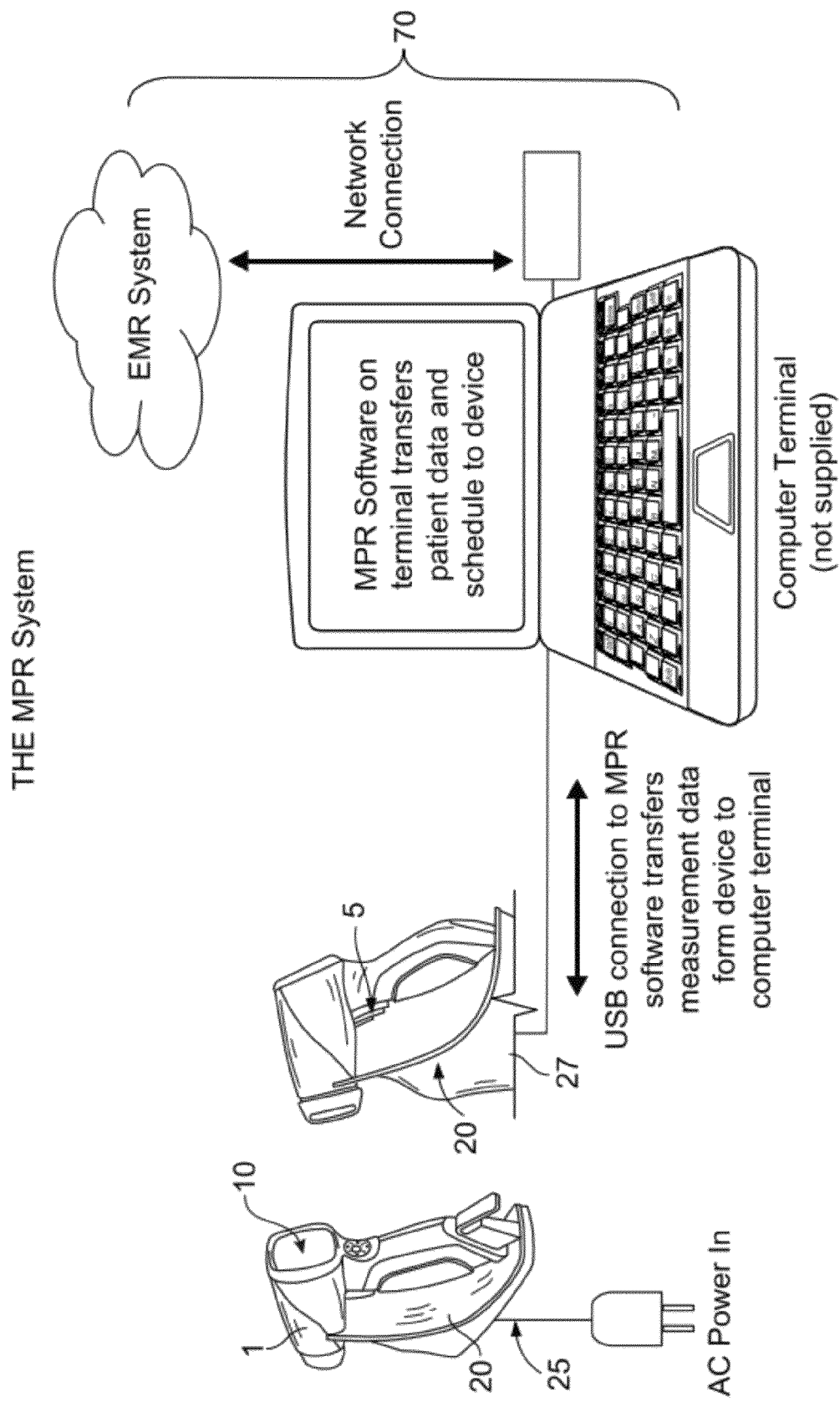
FIG. 3 is an illustration of a handheld macular pigment system.

FIG. 3 illustrates the handheld macular pigment reflectometer system in which the handheld macular reflectometer 1 is self-contained and can recharge its battery 22 from the base docking station 20. The battery 22 is used to provide power to the various components (e.g., the display 10, the CCD 50, the CCD 55, the first light source 12, the light engine 30, the spectrometer 35, motor for moving Badal lens or lenses 45, the Common path objective lens 120, motors for moving the first and second flip in-out mirrors, etc.) through the drive circuitry 24. By being battery-operated, the wireless handheld device 1 is more easily maneuvered by the operator when conducting the testing on the patient. The base station 20 includes an AC Power-in port 25 for charging the battery. Further, the handheld macular pigment reflectometer 1 communicates with an electronic medical records system 70 accessible by a computer using a USB connection 27, which is part of the base docking station 20. The electronic medical records system 70 may be resident within the computer, or it may be accessible via the computer through an extranet or intranet connection. Furthermore, it should be noted that the base station 20 may have a wireless connection to the computer, or a direct connection to a local or remotely located electronic medical records system 70 (such that a computer is not needed). Utilizing a device like the handheld macular reflectometer 1 for collecting eye-health data for use in diagnosing conditions and recording information in a large-scale database is disclosed in U.S. Publication No. 2010/0241450, which is herein incorporated by reference in its entirety. If used in such a system, the handheld macular reflectometer 1 would be connected to the computer and the computer would be used to enter details about the patient's information and background to create patient file, as shown in U.S. Publication No. 2010/0241450. The output of the handheld macular reflectometer 1 would then be sent to the computer and stored in association with the patient's file.

Figure 4:
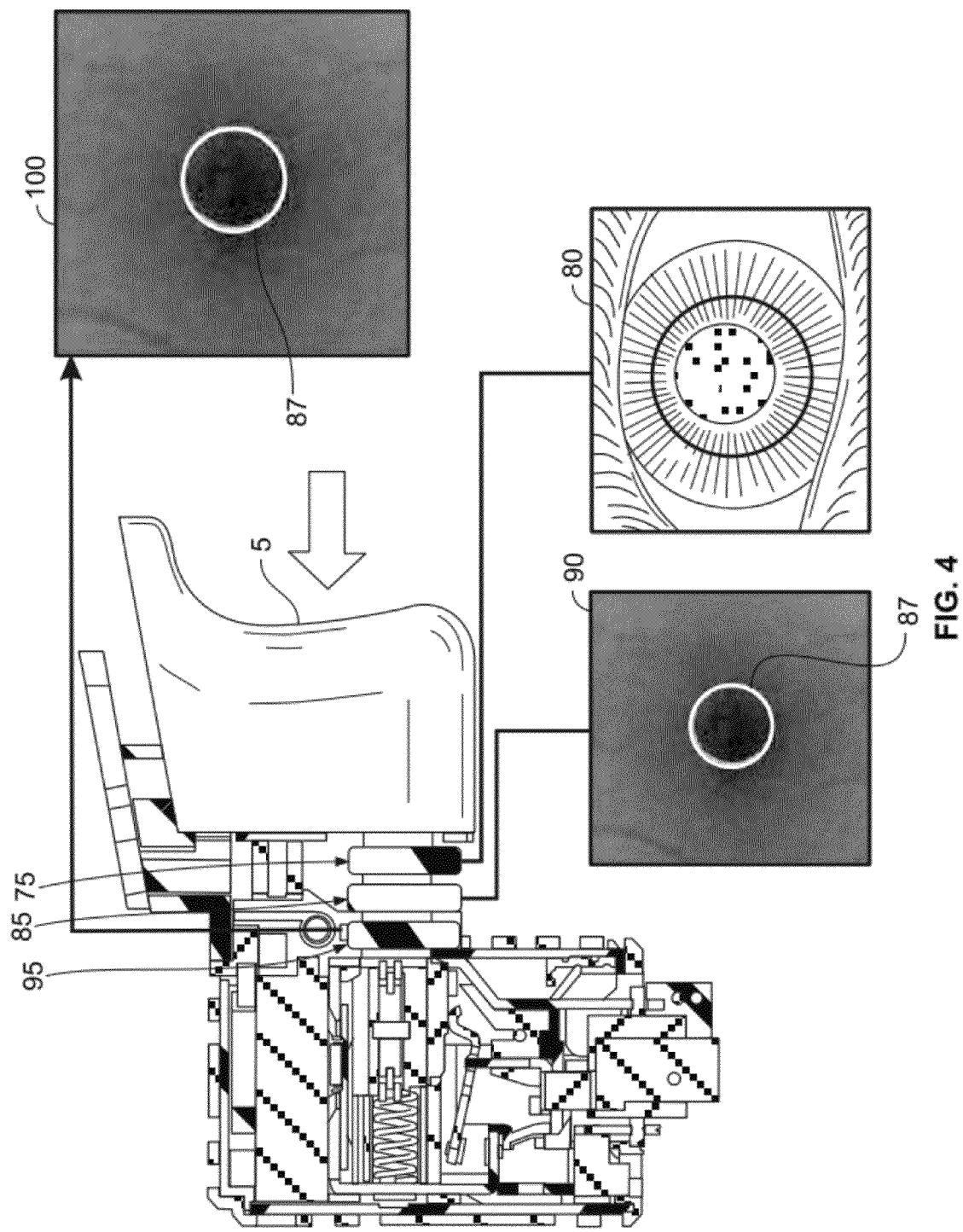
FIG. 4 is an illustration of a three-step trigger switched actuated instrument alignment.

FIG. 4 illustrates more of the details of the three-step actuation of the trigger 5 and the output on the display 10 during alignment process. The three-step actuation preferably includes some type of tactile feedback, such that the clinician feel this trigger 5 move between the three defined positions associated with electrical switches, each of which provides a signal corresponding to that particular trigger switch position. However, the tactile feedback is very subtle in nature, so as not to impede the motion of the trigger as it moves through its three positions and thus not upset the precise alignments achieved in the first, second and third trigger switch positions. In the first trigger switch position 75 (shown in FIGS. 2b, 5a and 5b), the handheld MPR instrument 1 maintains a wide-field anterior image 80 on the display 10 with a central obscuration aligned with the eye pupil. In the second switch position 85 (FIGS. 2c, 6a, 6b, 6c), there is a 4-degree central retinal field of vision 90 on the display 10 with a circular reticule 87 colored green, indicating a 1.0-degree central measurement area. In the third switch position 95 after the light engine 30 is operated in the pulsed condition (FIGS. 2d, 7a, 7b, 7c), the handheld MPR instrument 1 freezes the 4-degree image 100, ramps up the light engine 30, takes a white balance reading, actuates the second flip in-out mirror 67, activates the spectrometer 35, turns the reticule 87 to a red color, and flashes the reticule 87 in the image 100 if the trigger 5 is held for more than one second.

Figure 5A:
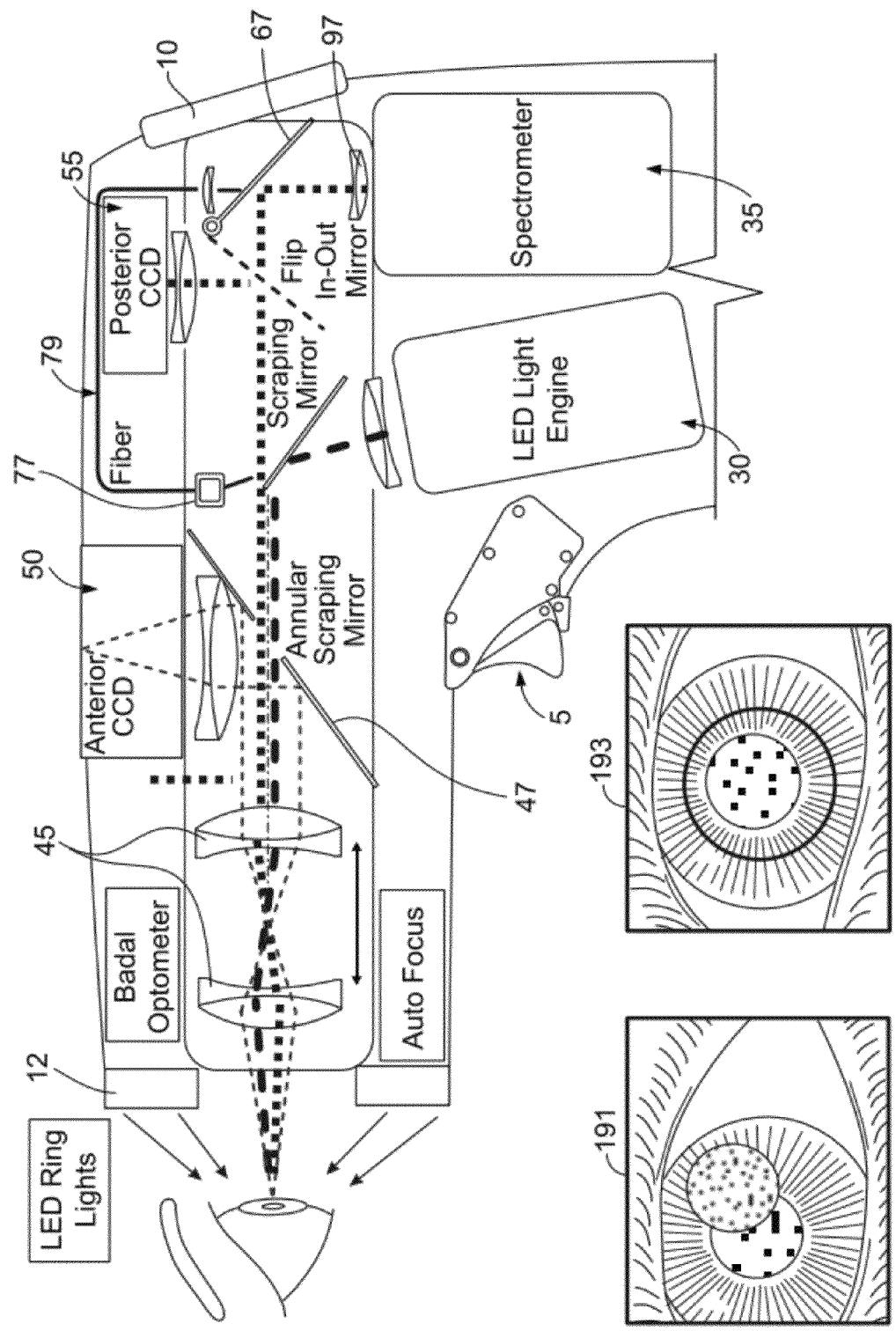
FIG. 5a is an illustration of the first position of the trigger switched actuated alignment, according to one embodiment.

FIG. 5a illustrates the active optical elements of the handheld macular pigment reflectometer 1 when the trigger 5 is in the first position. In the first position, the LED ring lights 12 illuminate the eye; the Badal Optometer 45 focuses return light through the annular scraping mirror 47 onto the anterior CCD 50, which is coupled to the display 10. The annular scraping minor 47 produces central obscuration. While the trigger 5 is in the first position, the central obscuration may not overlap the central pupil of the patient's eye as shown in image 191. The spectral ring is partially to completely invisible in the image 191 and it is not possible to view the retina upon transition. When the handheld MPR instrument 1 is slightly adjusted and the image central obscuration aligns with the natural pupil of the subject's eye as show in image 193 on the display 10, a sharp specular reflection of the illuminating LED ring 12 off the subject's cornea appears. When both conditions exist, this will result in a non-vignetted 4-degree retinal field of view upon transition. In one embodiment, the light engine 30 may blink or modulate at a low power during this time to (i) provide a fixation light for the patient to steady his or her gaze, and (ii) to provide a white reference beam to the spectrometer 35 through the fiber optic pickoff 77 and the fiber 79. In this situation, the posterior CCD 55 would be turned off, such that it will not matter if a small amount of return light strikes it.

Figure 6A:
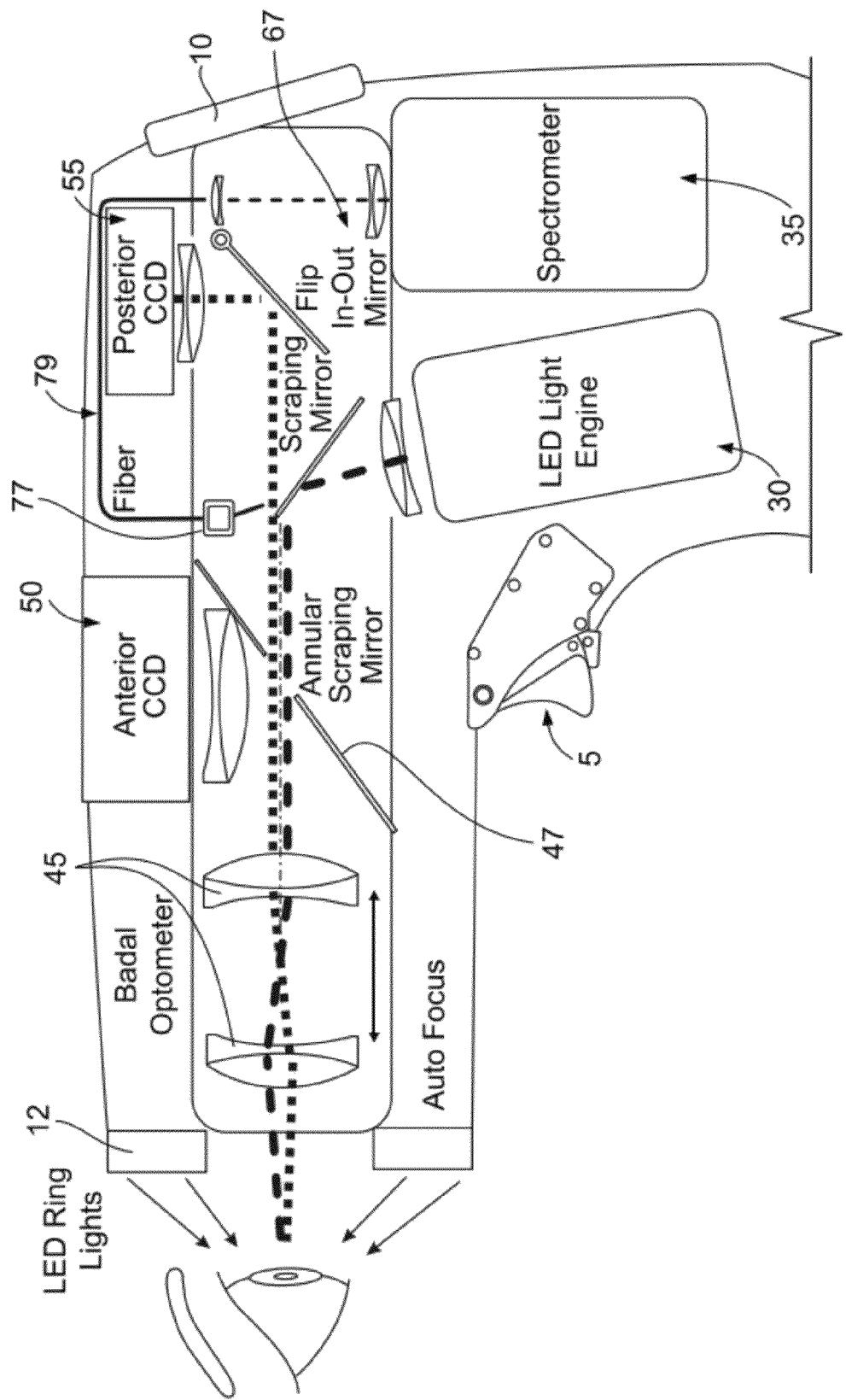
FIG. 6a is an illustration of the second position of the trigger switched actuated alignment, according to one embodiment.

FIG. 6a illustrates the macular pigment reflectometer 1 with the trigger 5 in the second position, which occurs as the operator continues to squeeze the trigger 5. In this position, the anterior CCD 50 and LED ring lights 12 shut down, and the LED light engine 30 begins operation. The Badal optometer 45 then switches to a refraction-correction mode, the flip-in mirror 67 remains in the "IN" position, and the posterior CCD 55, which is coupled to the display 10, becomes active. An image 145 with a 4-degree by 4-degree field of view is shown in the display 10 (FIG. 6d). The clinician aligns the handheld MPR instrument 1 until the patient's fovea centralis is located within the 1.0-degree circular reticule 87.

FIG. 7a illustrates the macular pigment reflectometer 1 after the trigger 5 has been advanced to the third position. In this position the flip-in minor 67 moves to the "OUT" position, the image on the posterior CCD 55 freezes, the Badal optometer 45 freezes, the LED light engine 30 increases in intensity and creates the pulsed output for 0.25 seconds and the return light is received by the spectrometer 35. The spectrometer 35 takes multiple spectral samples, such as five measurements in 0.25 seconds and averages them. To reduce the spectral noise, various techniques could be used, such as boxcar averaging or polynomial smoothing. Because the on-board spectrometer 35 captures spectra in very short intervals of time, there is less relative motion during spectral capture and the handheld MPR instrument 1 is more likely to be aimed at the fovea during capture.

Figure 7B:
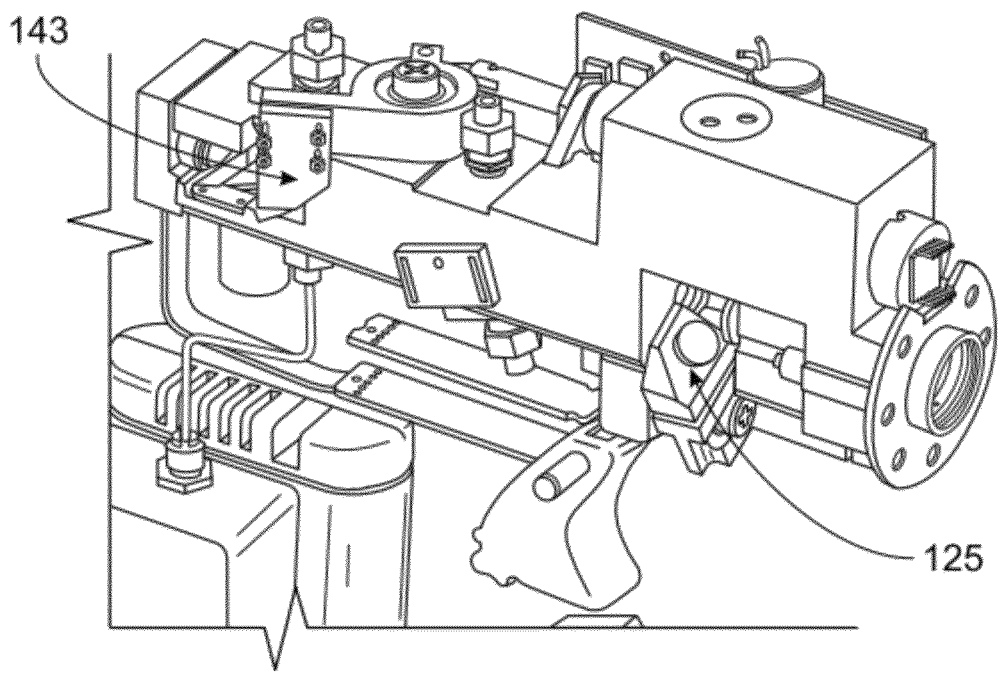
FIG. 7b is an illustration of another embodiment of the hand-held macular pigment reflectometer corresponding to the second position of the trigger switched actuated alignment and showing the first flip in-out mirror in its "OUT" position.
Figure 7C:
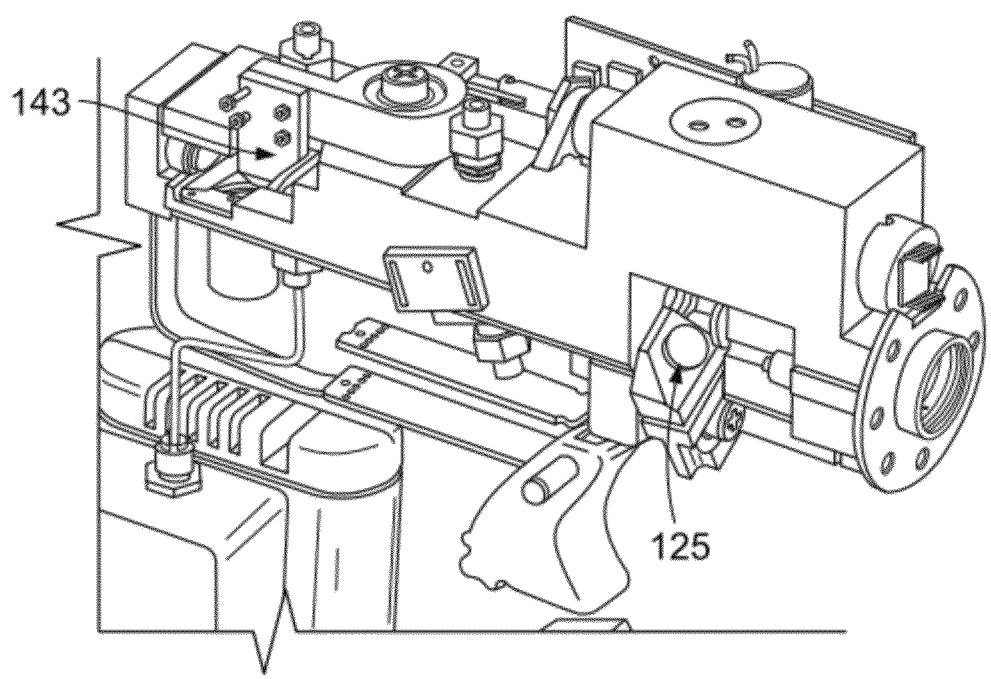
FIG. 7c is an illustration of the reflectometer of FIG. 7b showing the second flip in-out mirror in its "IN" position.
Figure 7D:
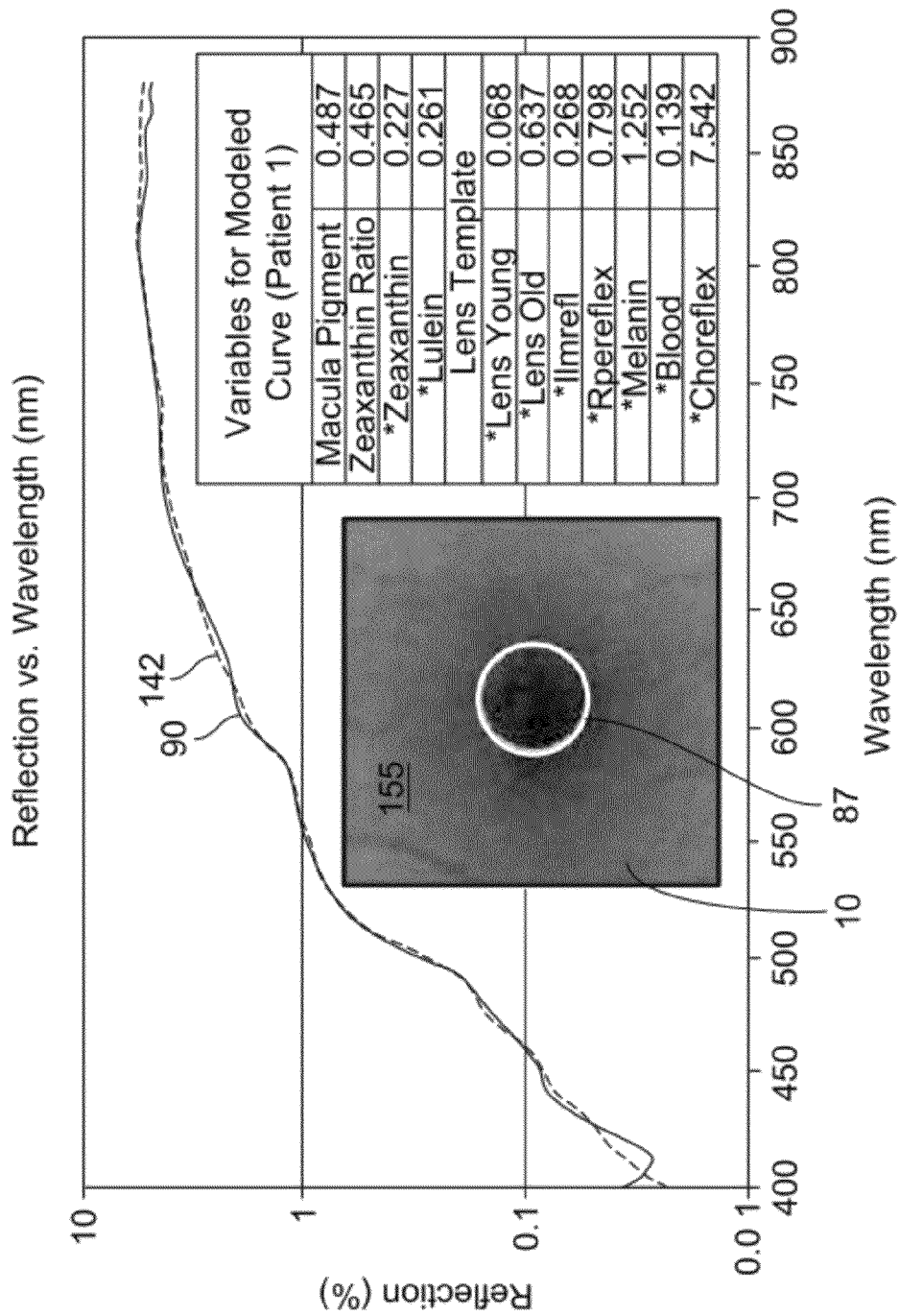
FIG. 7d is an image of a 4-degree field of view of a human retina and a graph of the reflection vs. wavelength.

As shown in the image 155 on the display 10 of FIG. 7d, the reticule 87 on the display 10 turns red. If the trigger 5 is held in the third position for more than one second, the reticule 87 begins to flash on the screen 10. The handheld MPR instrument 1 then calculates optical density, zeaxanthin optical density and lutein optical density. These values are typically reported after the trigger 5 is released. The handheld MPR instrument 1 can simply store the raw data and allow the connected computer or medical records system to calculate the values, or the handheld MPR instrument 1 may have the on-board processing to permit the calculation of the zeaxanthin optical density and lutein optical density. The details of the curve-matching functions used to determine the variables for the modeled curve are set forth in U.S. Pat. No. 7,467,870, which is herein incorporated by reference in its entirety.

According to the embodiment described above, the handheld MPR instrument 1 is designed to provide for two optical paths that are generally coaxial and concentric. An outer anterior optical path is annular in design both from an illumination and imaging function. An interior posterior optical path is within the outer optical path. The scraping mirror 58 is used to generate the posterior viewing and measurement path, by directing some 85% of the light generated by the LED light engine towards the patient's eye. The light directed towards the patient's eye will be slightly (about 1-2 degrees) off axis. This is to prevent specular reflections from the optical elements and the patient's cornea from reflecting back into the spectrometer optical path. The other 15% not directed to the patient will be directed into the pickoff fiber optic 77, which is used to periodically make a white reference measurement with the spectrometer 35. When the flip-in mirror 67 is in the IN position, the white reference can be detected, if required. When the mirror 67 is in the OUT position, the mirror 67 will block the 15% leaked light from the light engine 30 from reaching the spectrometer 35, only light that has reflected off the patient's retina will be permitted to reach the spectrometer. Annular optical systems typically leave a central obscuration at the image plane. In this application, the obscuration is not detrimental to the function of the anterior image, and in fact can be used to facilitate alignment for rapid transition to the posterior image. Except for within the Badal Optometer refractive power correcting elements 45, each optical path is separate from the other. The Badal optometer 45 serves two distinct purposes, depending on the viewing mode. In the anterior mode, the Badal optometer 45 acts as an autofocus mechanism, and a motor drives one of the lens elements (e.g. the posterior lens) to compensate for slight motions of the patient or instrument. The relative motion of the lens in this mode is quite small, typically less than 200 um total travel. However, the bandwidth of the motion is relatively high, approximately 5 Hz. When the viewing mode switches to the posterior mode, the Badal optometer 45 functions more as a typical refractive power corrector. The Badal optometer 45 is moved to a position corresponding to the net refractive power error of the patient. This motion could be as far as 1.5 mm for a >15 Diopter correction. Then, from this new position, the lens group 45 returns to a small motion high bandwidth autofocus function, but for the posterior CCD 55. The annular scraping mirror 47 spatially separates the two paths. The hole in the annular scraping mirror 47 will determine, in large part, the central obscuration. It is also the limiting aperture for the retinal imaging optics. And, as described above, each optical path has its own detector, the anterior CCD 50 and the posterior CCD 55.

It should be noted, according to some embodiments, that the handheld MPR instrument 1 preferably includes a stabilizing lens 97, to help stabilize the light going to the spectrometer 35. The stabilizing lens 97 can be a fluidic lens or based on a LensVector autofocus technology (e.g., lens on MEMS) from LensVector, Inc. of Mountain View, Calif.

Figure 2B:
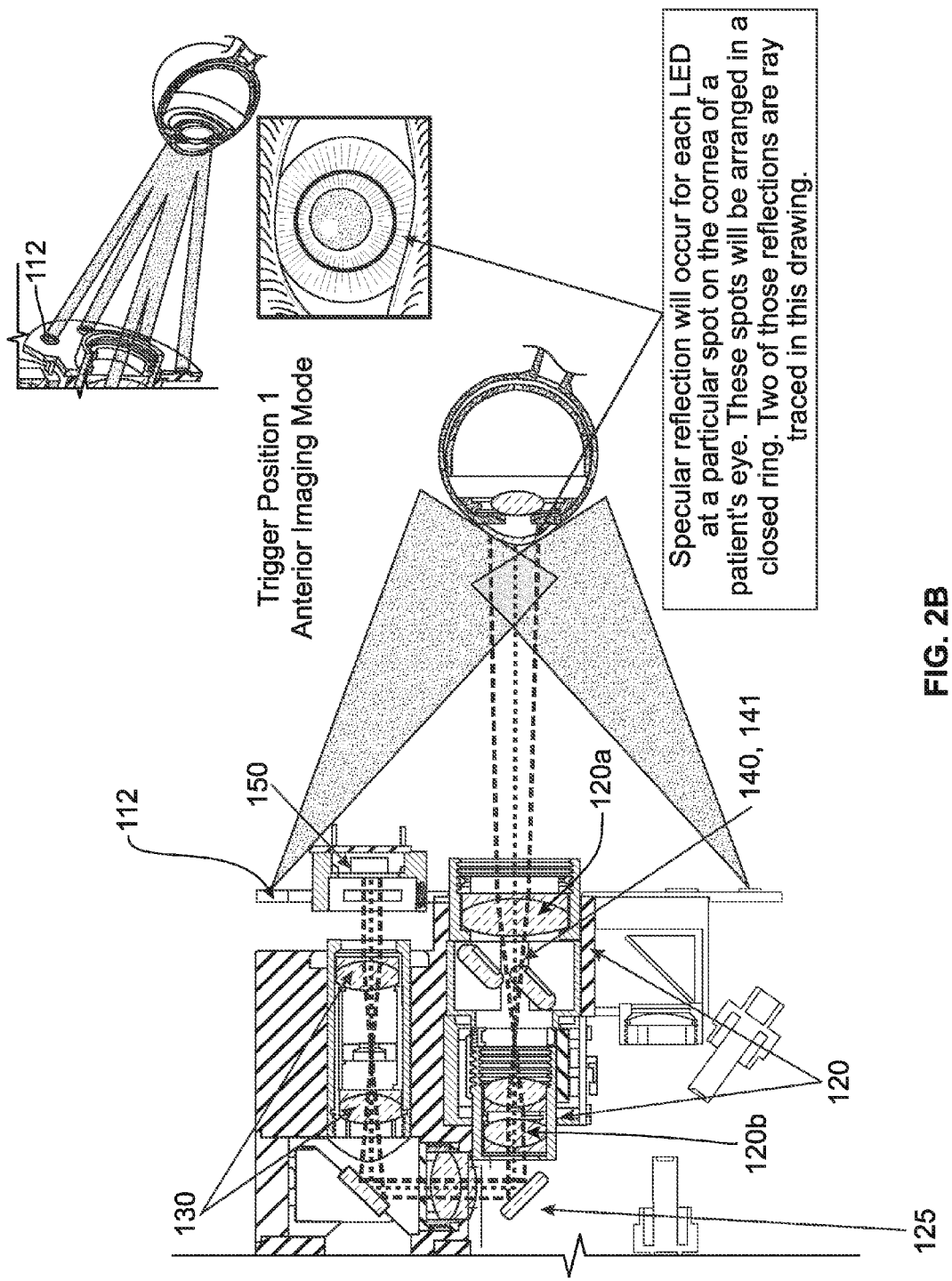
FIG. 2b is a schematic drawing of the hand-held macular pigment reflectometer, according to another embodiment, illustrating the anterior imaging mode, trigger position 1.
Figure 2C:
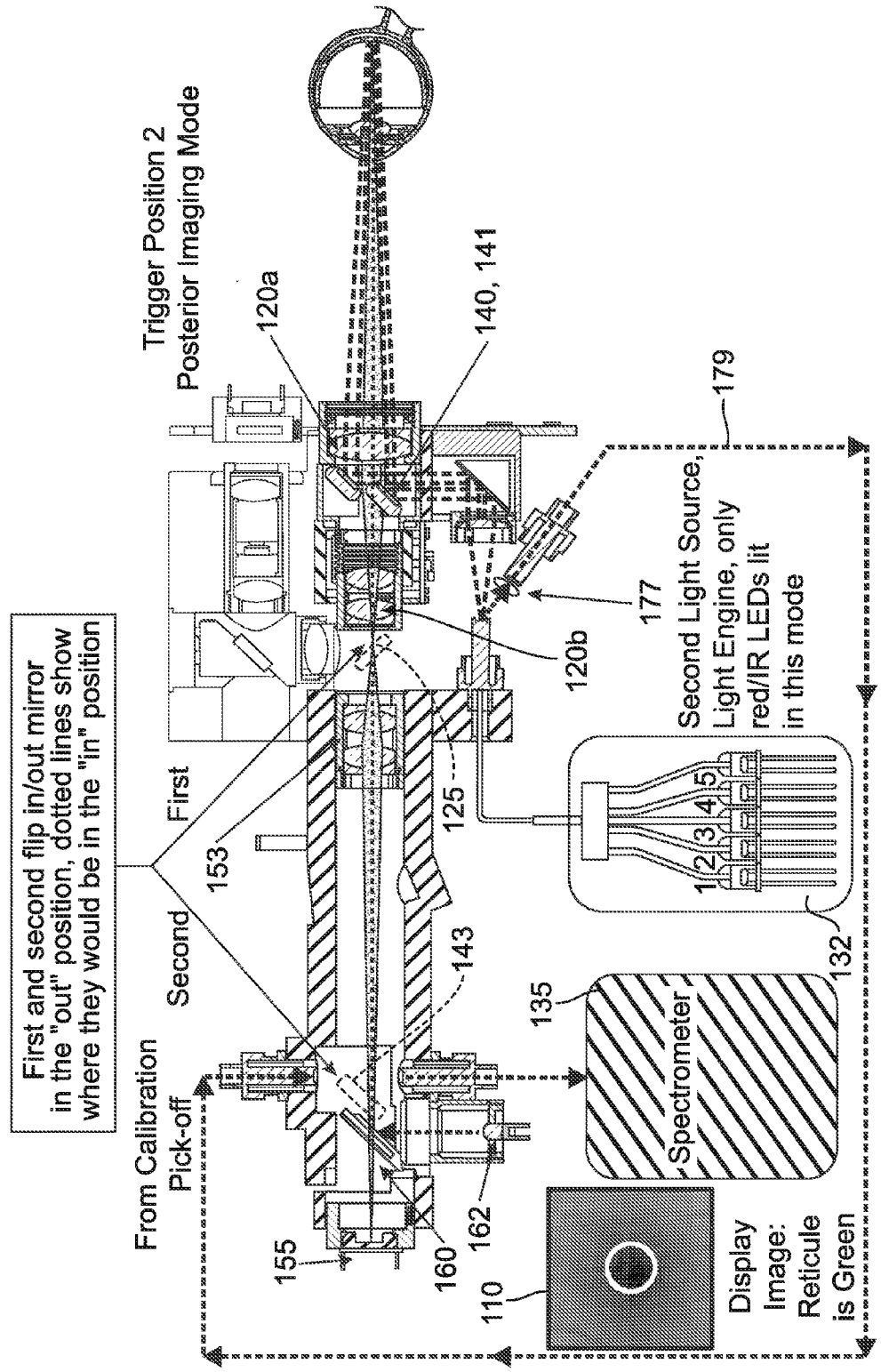
FIG. 2c is a schematic drawing of the hand-held macular pigment reflectometer of FIG. 2b, illustrating the posterior imaging mode, trigger position 2.
Figure 2D:
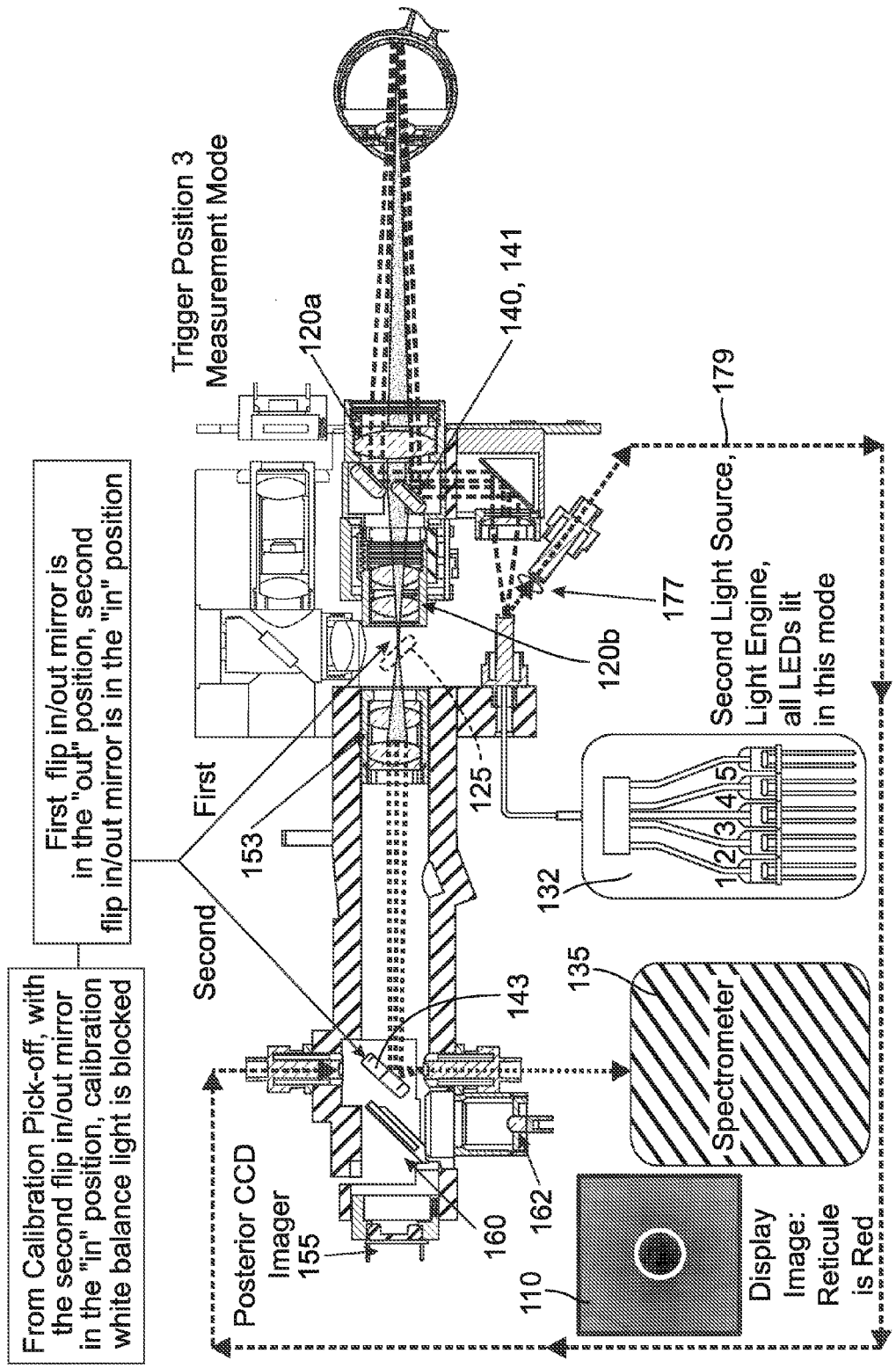
FIG. 2d is a schematic drawing of the hand-held macular pigment reflectometer of FIG. 2b, illustrating the measurement mode, trigger position 3.

A further embodiment of the hand-held reflectometer is shown in FIGS. 2b-d. These drawings illustrate a sequential series of light paths that correspond to a three-step alignment method, which corresponds to a first trigger switch position, a second trigger switch position and a third trigger switch position of the hand-held MPR. The hand-held MPR instrument 101, shown in FIG. 2b, contains a first light source 112 that is preferably arrayed in a ring within an eye cup or eye shield 115 and preferably utilizes LED illumination. The first light source 112 creates both a specular reflection from the cornea that is used in the alignment process and a diffuse reflection that is used to image the entire anterior portion of the eye. As shown in FIG. 2b, diffuse and specular light reflected from the anterior portion of the eye is captured, focused and relayed by a Common path objective lens 120 back to a first flip in-out mirror 125. The Common path objective lens 120 consists of two lens groups, with a first lens group 120a being fixed relative to the second lens group 120b. In a preferred embodiment, the second lens group 120b is moveable via a small motor. This first flip in-out mirror 125 relays the image through a focusing lens group 130 to an anterior charge coupled device (CCD) imager 150. The images captured by this CCD imager 150 are displayed on screen 110 and used for initial alignment of the handheld MPR instrument 101. The light from the first light source 112, corresponding to the first trigger switch position, preferably corresponds to spectra in the range of 680-900 nm, and preferably 880 nm.

Figure 8:
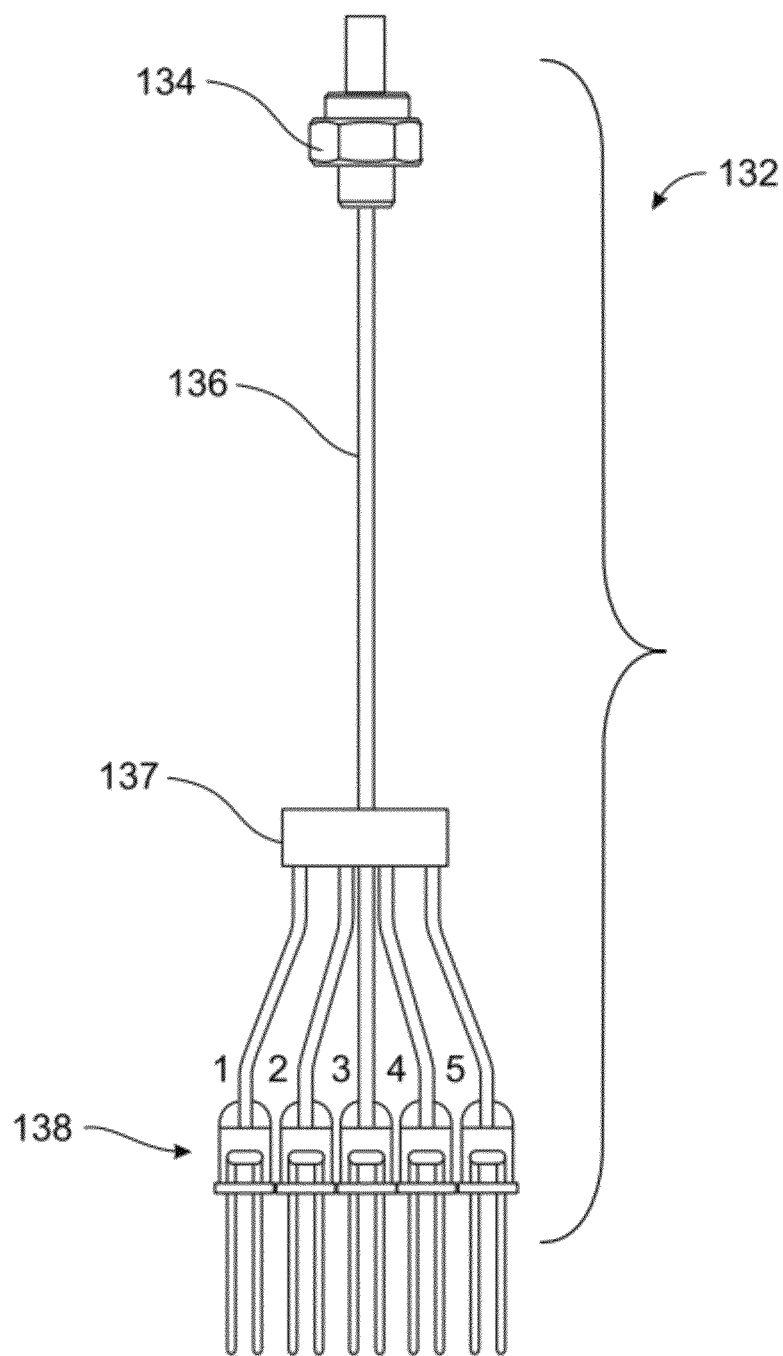
FIG. 8 is an illustration of a second light source LED or light engine according to one embodiment.

As the trigger 105 is further pulled to its second position as shown in FIG. 2c, the first light source (ring LED) 112 is shut down, the first flip in-out mirror 125 is moved to the "OUT" position, and a second light source or light engine 132 is initiated. This second light source or light engine 132 is preferably a combination of a plurality of LEDs (e.g., five LEDs) that, when spectrally combined, provide a spectral range from 400 nm to 880 nm, and more preferably in this mode, in the range of 630-880 nm. FIG. 8 illustrates an example of one type of light source that provides the desired spectral range. The light at this point in the alignment process is preferentially red and infrared illumination from the red and infrared LEDs of the light engine 132 as shown in the spectra of FIG. 7d. Once the individual LEDs are ramped to their steady state position, the light from the second light source or light engine 132 is collimated, folded and directed to a chevron mirror 140 that divides the light into two beams, and directs those beams through the first lens group 120a of the Common path objective lens 120 to the eye. The reflected light passes through the first lens group 120a of the Common path objective lens 120 (which now acts as a focusing element), and on to the patient.

The light from the second light source or light engine 132 passes through the patient's cornea and lens, reflects off of the retina and returns back through the eye's optics to the handheld MPR instrument 101. The area illuminated on the retina is about 1.0 mm in diameter, which is approximately 4 degrees of angular sub tense. In particular, the reflectance curve from this region of the retina shows the contributing factors of absorption of the carotenoids, lutein and zeaxanthin. The reflectance and absorption of the light in the eye is described in more detail in FIG. 7d and in U.S. Pat. No. 7,467,870, which is herein incorporated by reference in its entirety.

Light returning to the handheld MPR instrument 101 now passes back through the same optics from which it came, except that the returning light will now pass in between chevron mirrors 140 and 141, and miss entirely the second flip in-out mirror 143 in its "OUT" position, and be re-imaged by a posterior optical group 153 to a posterior CCD imager 155. In response to the reflected energy being received by the posterior CCD imager 155, a 4 degree image of the macula is formed and displayed on the screen 110. Further alignment by the clinician may be anticipated, but getting the pupil aligned first (via the anterior alignment accomplished in the first trigger switch position), significantly eases the alignment task. Patient comfort is maximized by utilizing only the red and infrared LEDs while in the second trigger switch position, and the retinal pigments (rhodopsin) are bleached to a precisely known condition, which can be optimized by the posterior illumination light levels. This condition is described in more detail in the *Journal of the Optical Society of America*, "Effect of wavelength on in vivo images of the human cone mosaic," Vol. 22, No. 12, December 2005, which in incorporated herein in its entirety. The patient will also be provided a low intensity blue fixation light 162, which will contrast with the red posterior illumination light from the LED light engine 132. The fixation light 162 is preferably a blue 440 nm low intensity LED, which is collimated, diffused and apertured so as to subtend a small angular space to the patient. It is folded into the optical path by a dichroic beamsplitter 160.

Meanwhile, while the eye is being aligned, the light from the secondary light source or light engine 132 (2% of the output from the second light source or light engine) that is not being collimated and directed to the chevron mirrors 140, 141 passes on to a small collection optic 177 and into a fiber 179, which re-directs it to the spectrometer 135. This light is available and can be checked by the spectrometer 135 periodically, and sets the "white balance" or native spectral signature for the second light source or light engine 132 for the spectrometer 135.

Figure 10:
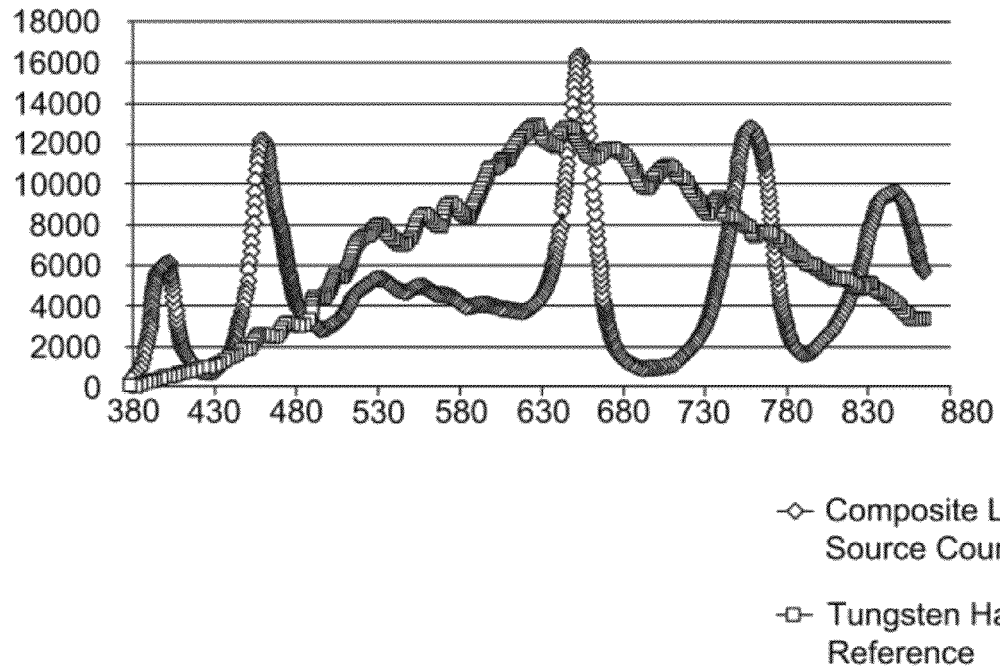
FIG. 10 is an illustration of the illumination spectra for the measurement of macular pigment, 1-degree field of view (third trigger switch position).

Once the eye is aligned and in focus, the trigger switch 105 is pulled to its third and final position, as shown in FIG. 2d. The second light source or light engine 132 ramps up to its measurement condition, which includes all LEDs in the light engine illuminated at a spectrally optimal condition as shown in FIG. 10, and which provides a pulse of energy, such as a few hundred millisecond pulse of light that will be approximately three times the brightness as the steady-state condition when the trigger switch 105 is in the second position. As this occurs, the first flip in-out minor 125 remains in the "OUT" position, and the second flip in-out minor 143 moves to the "IN" position which will block the "white-balance" light from the fiber 179, but will allow for all light that normally would be incident upon the posterior CCD 155 to now enter the spectrometer 135 (through some collection optics, including a short fiber, not shown). In the third trigger switch position, the higher intensity broadband illumination is in the range of 400-880 nm. The fixation LED 162 is shut down for this brief period, and the display 110 is frozen on the last frame of the posterior imaging mode, but the green reticule displayed has been changed to a red reticule.

The spectrometer 135 takes a plurality of spectral readings, such as five sequential spectra that are 50 milliseconds each, during the few hundred millisecond measurement period. The spectrometer 135 and microcomputer (not shown) sorts the spectra for a variety of reject criteria, and of the spectra it keeps, will average them and calculate the lutein optical density (LOD), the zeaxanthin optical density (ZOD), and the combined macular pigment optical density (MPOD). The method of calculation is well detailed in U.S. Pat. No. 7,467,870, which is incorporated herein by reference in its entirety.

The numbers will displayed on display 110 to the clinician, and saved in memory in a microcomputer system (not shown). The clinician releases the trigger switch 105 and can repeat the procedure, as necessary. The detail of analysis that determines these density values is set forth in U.S. Pat. No. 7,467,870.

Figure 5B:
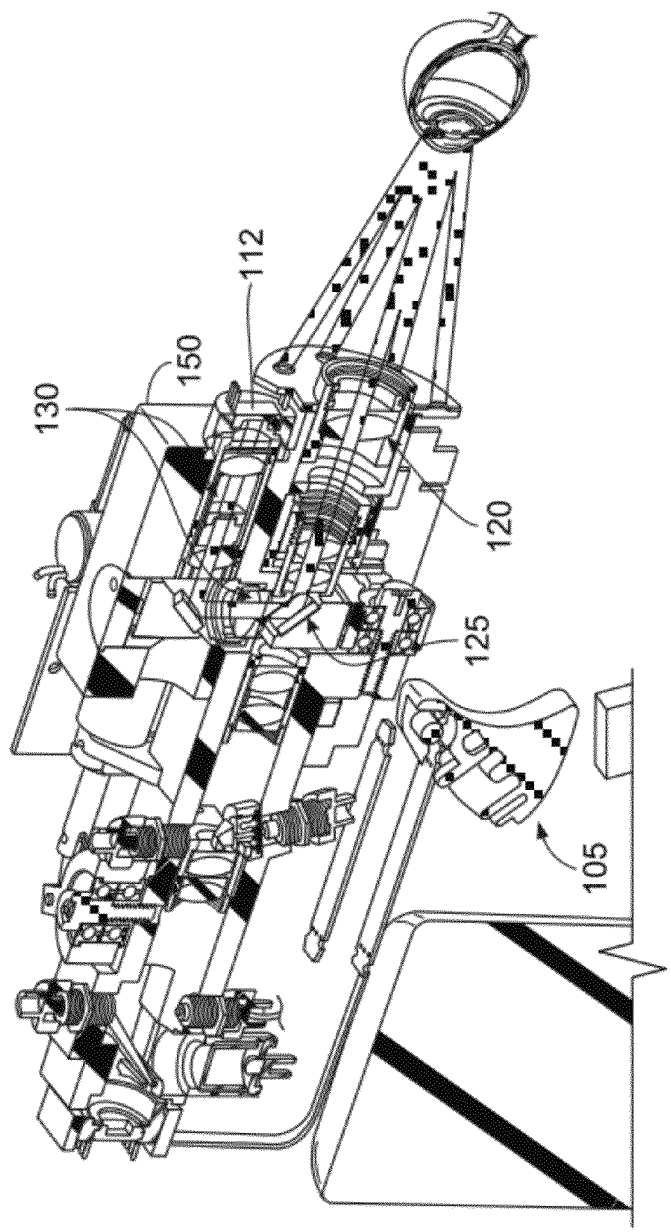
FIG. 5b is an illustration of another embodiment of the hand-held macular pigment reflectometer corresponding to the first position of the trigger switched actuated alignment and showing the anterior light path.
Figure 5B:
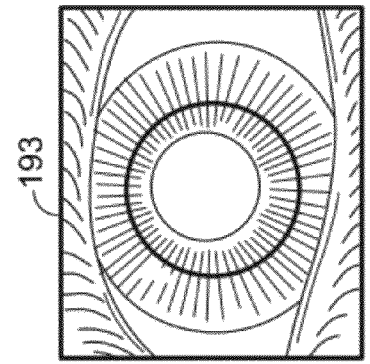
Figure 5B:
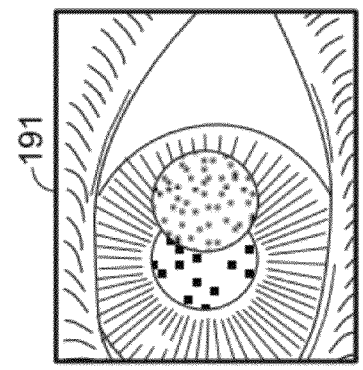

The first trigger switch position, corresponding to the anterior light path, is further illustrated in FIG. 5b (as well as shown in FIG. 2b). As noted above, in the first trigger switch position, the first light source 112 (LED ring lights) illuminates the eye, the Common path objective lens 120 focuses return light through the first flip in-out minor 125 and relays optics onto the anterior CCD 150, which is coupled to the display 110. As noted above, while the trigger switch 105 is in the first position, the central obscuration may not fully overlap the central pupil of the patient's eye as shown in image 191. The spectral ring is partially to completely invisible in the image 191 and it would not be possible to view the retina upon transition. When the handheld MPR instrument 101 is slightly adjusted and the image central obscuration aligns with the natural pupil of the subject's eye as show in image 193 on the display 110, a sharp specular reflection of the illuminating LED ring 112 off the subject's cornea appears. When both conditions exist, this will result in a non-vignetted 4-degree retinal field of view upon transition. In one embodiment, the light engine may blink or modulate at a low power during this time to (i) provide a fixation light for the patient to steady his or her gaze, and (ii) to provide a white reference beam to the spectrometer 135 through the fiber optic pickoff 177 and the fiber 179. In this situation, the posterior CCD 155 is turned off.

Figure 6B:
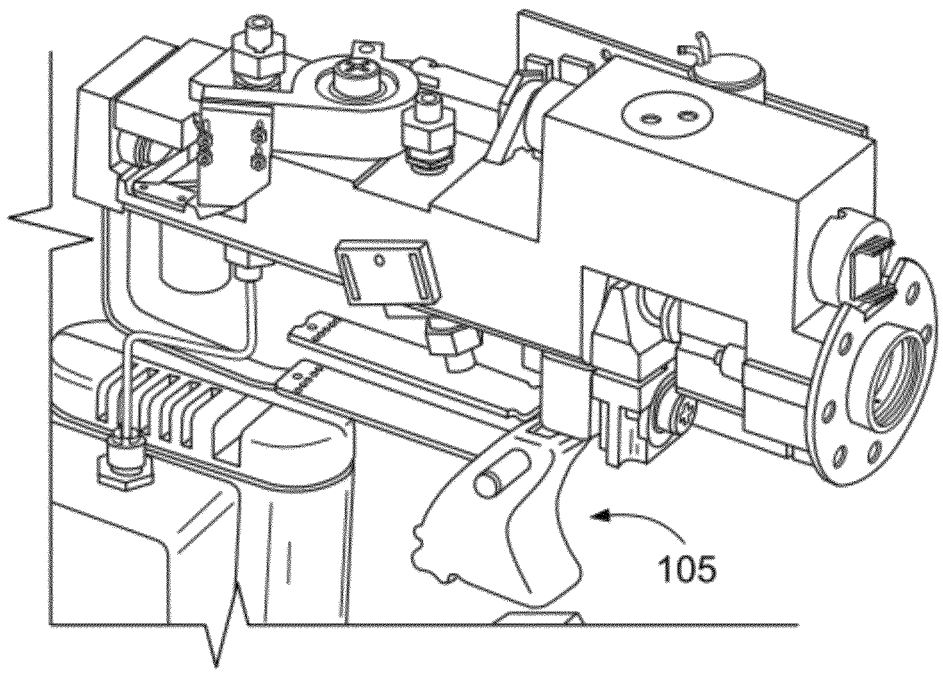
FIG. 6b is an illustration of another embodiment of the hand-held macular pigment reflectometer corresponding to the first position of the trigger switched actuated alignment and showing a first flip in-out mirror in its "IN" position.
Figure 6C:
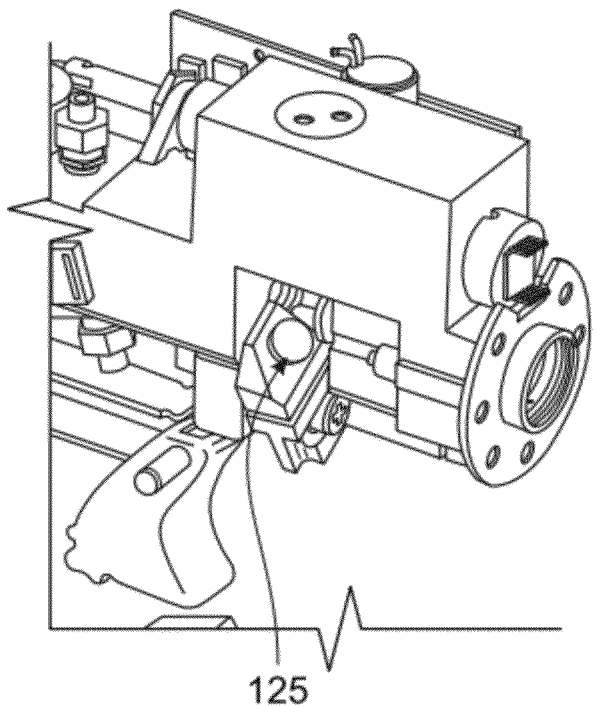
FIG. 6c is an illustration of the reflectometer of FIG. 6b showing the first flip in-out mirror in its "OUT" position, illustrative of the second trigger position.
Figure 6D:
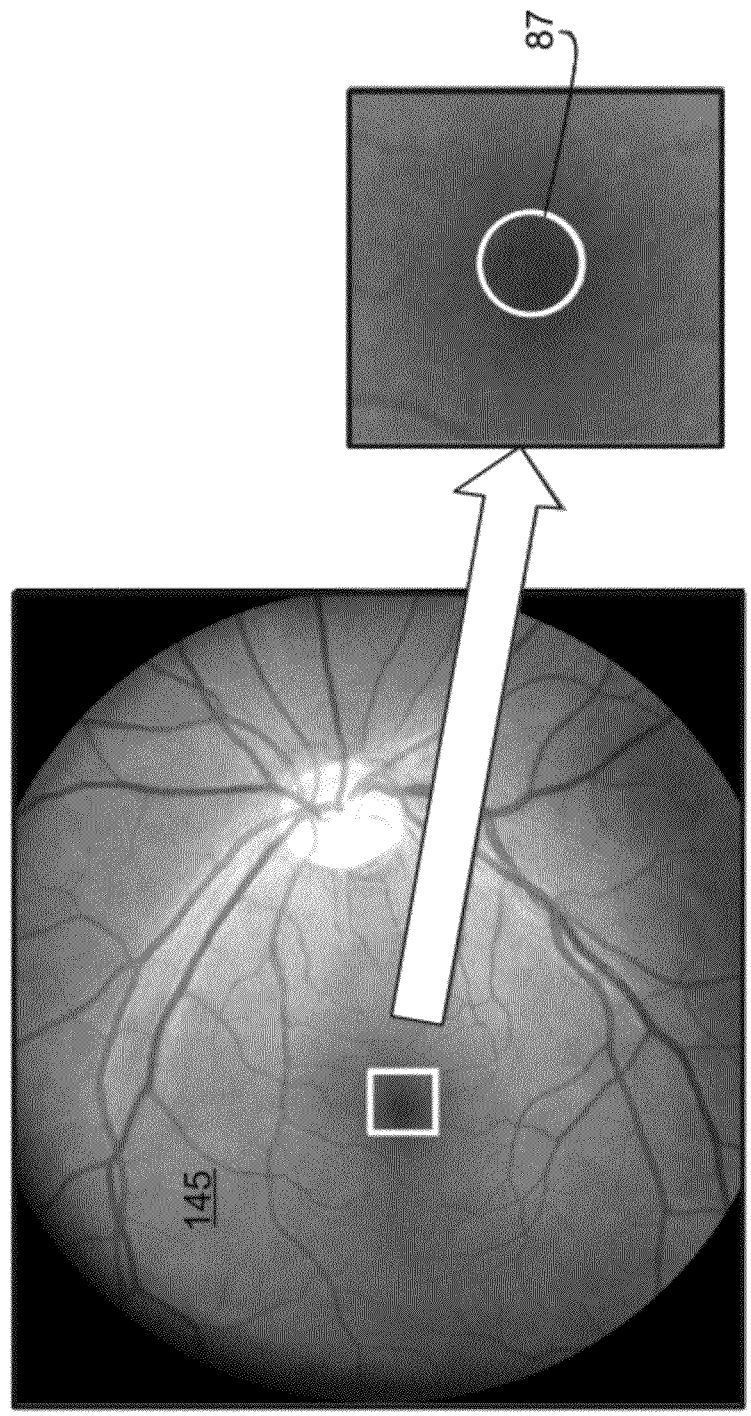
FIG. 6d is an image of a human retina and a corresponding 4-degree field of view.

The second trigger switch position, corresponding to the posterior light path, is further illustrated in the transition from FIG. 6b to FIG. 6c. The second trigger switch position occurs as the operator continues to squeeze trigger switch 105. In this position, the anterior CCD 150 and first light source (LED ring lights) 112 shut down, and the second light source or light engine 132 becomes the predominant light source. The first flip in-out minor 125 moves from its "IN" position to its "OUT" position (see FIG. 6c), and the posterior CCD 155, which is coupled to the display 110, becomes active. An image 145 with a 4-degree by 4-degree field of view is shown in the display 110 (FIG. 6d). The clinician aligns the handheld MPR instrument 101 until the patient's fovea centralis is located within the 1.0-degree circular reticule 87.

The transition from FIG. 7b to FIG. 7c further illustrates the posterior illumination measurement path corresponding to the third trigger switch position. In this position, the second flip in-out mirror 143 moves from the "OUT" position to the "IN" position (see FIG. 7c), the image on the posterior CCD 155 freezes, the Common path objective lens 120 freezes, the LED light engine 132 increases in intensity and creates the pulsed output for several hundred milliseconds and the return light is received by the spectrometer 135. The spectrometer 135 takes multiple spectral samples or measurements, such as five measurements in 0.25 seconds, and averages them. To reduce the spectral noise, various techniques could be used, such as boxcar averaging or polynomial smoothing. Algorithms within the microcomputer compare each spectra to a known modeled or "good" spectra, and any spectra not within a pre-determined tolerance band of the known good spectra are considered "bad" spectra or data, and are filtered out of the set and rejected. FIG. 7d shows a modeled spectra 90 and an actual measured spectra 142. Spectra 142 would be considered acceptable data because it is within the tolerance bands of the algorithm. Because the on-board spectrometer 135 captures spectra in very short intervals of time, there is less relative motion during spectral capture and the handheld MPR instrument 101 is more likely to be aimed at the fovea during capture.

According to the embodiment described above (particularly in FIGS. 2b-d, 5b, 6b-c and 7b-c), the handheld MPR instrument 101 is designed to provide for two optical paths that are partially coincident. An anterior optical path provides both an illumination and imaging function. A posterior optical path utilizes the Common path objective lens group of the anterior optical path. The first flip in-out mirror 120 is used to separate the anterior and posterior viewing and measurement paths, by directing light reflected from the cornea and the anterior eye through relay optics to an optimized CCD imager 150. The light directed towards the patient's eye will be off axis. This is to prevent specular reflections (except from the cornea) from the optical elements and the patient's cornea from reflecting back into the imaging optical path. Light from the light engine will also enter the eye slightly off axis so as to avoid corneal, lenticular specular reflections. Light returning from the retina will minimize specular reflections to interfere with the image. Stray light from other sources is reduced or nearly eliminated by the use of the eye cup 115 surrounding the space between the instrument and the patient's eye.

Light not directed to the posterior illumination chevron mirror 140 will be directed into the pickoff fiber optic 177, which is used to periodically make a white reference measurement with the spectrometer 135. When the second flip in-out minor 143 is in the "OUT" position, the white reference can be detected, if required. When the second flip in-out minor 143 is in the "IN" position, the second flip in-out mirror 143 will block the white balance light from the light engine from reaching the spectrometer 135. Thus, only light that has reflected off the patient's retina will be permitted to reach the spectrometer. The anterior optical path is designed to facilitate alignment, both from an illumination and imaging function. This optical path typically leaves a central obscuration at the image plane. This obscuration can be created optically by masks, or electronically within the CCD image.

Except for within the Common path objective lens elements 120, each optical path is separate from the other. The Common path objective lens 120 serves two distinct purposes, depending on the viewing mode. In the anterior mode, the Common path objective second lens group 120b acts as an autofocus mechanism, and a motor drives this group to compensate for slight motions of the patient or instrument. The relative motion of the lens in this mode is quite small, typically less than 500 um total travel. However, the bandwidth of the motion is relatively high, approximately 5 Hz. The refractive power correction of the system is accomplished as described herein. In particular, the optical group consisting of the posterior view CCD, the fixation light and beamsplitter, the second flip in-out mirror and the spectrometer port (with corresponding white balance fiber input) all move together as a group along the optical axis. With the patient's refractive error known, the user dials in the refractive error by turning a knob which turns a lead screw. The lead screw is the active element of a mechanical stage which translates the group along the optical axis, depending on the intended refractive error to correct. For example, to correct for a +5 D refractive error, the optical path to the group will have to lengthen by approximately 15 mm. Similarly, a −5 D refractive error would be corrected by shortening the optical path to the group by 15 mm. This function is not shown in the figures.

FIG. 8 is an illustration of a second light source or light engine 132 that may be used with the present invention. This second light source or light engine 132 includes a SMA connector 134, a plastic optical fiber pigtail 136, a light mixer 137 and a plurality of fiber-coupled light emitting diodes 138. These plurality of LEDs 138 are combined together to emit a very broad spectrum of visible to near-infrared light, namely 400 to 880 nm. Typically 5 or more LEDs can be combined together to create a posterior light source (LED light engine), although more or less may be used. This combination of LEDs replaces the tungsten halogen lamp that was the core illuminator on tabletop designs. Besides being faster to warm up, more stable over the long term, longer lifetime, lower power consumption, lower heat production, more efficient than the tungsten halogen lamp, the light engine offers a novel attribute: rapid and programmable spectral modification.

As background, the tungsten halogen lamps' spectra can be modified, by both power applied and by the use of discrete optical filters. Modification of the spectra by power applied simply shifts the spectra by a few nanometers, the higher the power applied, the bluer the light. The modification of the spectra by filters is also commonly used. However, filters simply change the spectra in discrete steps, by attenuating portions of the tungsten halogen emission band. Filters increase the complexity and cost of the system by adding electro-mechanical components to move them in and out of the illuminator pathway. Filters can also potentially age with time, and thus change in their attenuating characteristics. Finally, as mentioned, filters only allow for discrete step function changes in spectra.

The LED light engine offers a fundamentally different approach. It allows for different illumination characteristics depending on the alignment state the instrument is in, and allows for those characteristics to be tuned for optimal performance. Thus, according to one non-limiting example, in the first trigger switch position, the light engine is off and only the fixation light from the posterior optics is illuminated. The anterior illumination ring is illuminated for the anterior view. In the second trigger switch position, the red portion of the LED engine is lit, to allow for illumination while the clinician navigates to the fovea. The blue fixation light is lit as well, but the exterior ring of LEDs is off and the blue and white LEDs of the light engine are turned off or way down in intensity, to allow for optimal patient comfort while the clinician aligns to the fovea. The illumination level in this mode is a balance between optimal illumination for patient comfort, return signal to the posterior sensor, and sufficient illumination to bleach the foveal cones of rhodopsin (retinal pigments) to a known and consistent state.

This will allow the algorithm that analyzes the retinal reflectance to determine the macular pigments to work at optimum conditions. In the third trigger switch position, the blue and white LEDs are illuminated in combination with the red and infrared LEDs to produce the full broad spectrum. These LEDs can be ramped up in intensity to adequate levels to allow the spectrometer optimal signal to noise ratio, balancing patient eye comfort and safety issues. See FIGS. 9 and 10 for examples of illumination spectra for the second and third trigger switch positions. The advantages of such a measurement approach are several. For example, less total power is consumed, the patient is more comfortable during the exam, less heat is produced and the measurement is fundamentally more consistent when the bleach levels of the cones are precisely controlled. This is important to a variety of ophthalmic measurements, not just macular pigment measurement. Autofluorescence and dye enhanced fluorescence could benefit in terms of improving background noise consistency from this illumination approach, as well as other reflectometry-based instruments (laser scanning ophthalmoscopes, retinal thickness analyzers, retinal blood flow analyzers, etc.) which would benefit in terms of background noise reduction.

Figure 9:
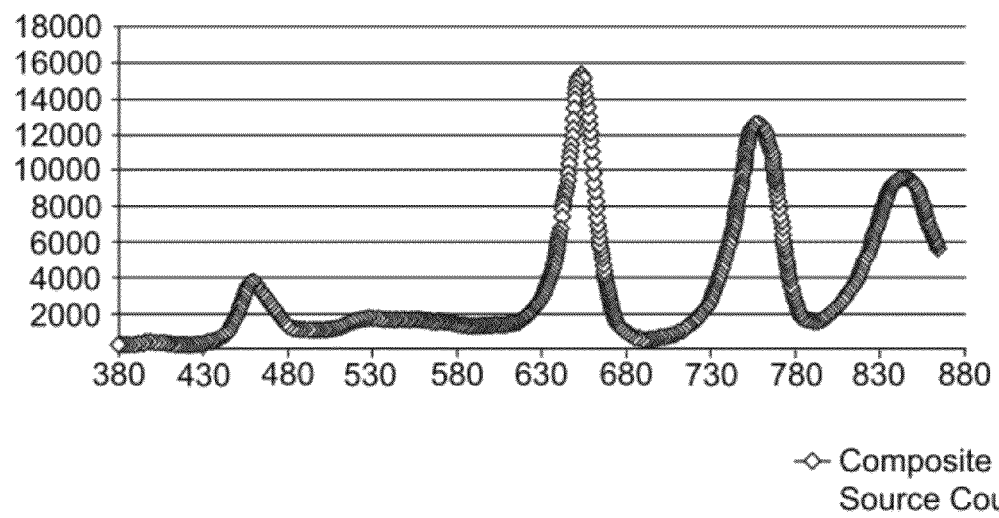
FIG. 9 is an illustration of the illumination spectra for the 4-degree field of view (second trigger switch position).

FIG. 9 is an illustration of the illumination spectra for the 4 degree field of view (second trigger switch position). This can be tuned with time to optimize the tradeoffs between patient comfort, instrument signal, and patient foveal cone bleach condition. In this position, only LEDs 3, 4 and 5 out of the LED light engine (see FIG. 8) are illuminated. LEDs 1 and 2 are barely emitting (i.e., "simmer" mode), but will allow for rapid transition to the third trigger switch position for taking a measurement.

FIG. 10 is an illustration of the illumination spectra for the measurement of macular pigment, one-degree field of view (third trigger switch position). This can also be tuned as a function of the tradeoffs mentioned above for FIG. 9, and also tuned in terms of the ramp up of the intensity of illumination.

Thus, as described herein, a handheld ophthalmic instrument with a unique human interface is provided, whereby a user can simply squeeze through a series of trigger switch positions to achieve a complex alignment and measurement procedure rapidly with minimal effort and unwanted instrument motion. The measurement procedure is comprised of three modes—an anterior alignment, posterior alignment, and spectroscopic measurement and calculation. Transition through the modes is seamless because of the trigger switch design as described herein.

Other advantages of the hand-held MPR as described herein include providing spectra that is different and optimized for each task. For example, according to one embodiment, infrared LED light (880 nm typically) is provided for illuminating the eye during anterior alignment to ensure the pupil of the eye stays large. Red (typically 635 nm) or green-red-IR (typically 530-880 nm) LED light is provided for illuminating the eye during posterior alignment, which ensures a comfortable illumination color to the patient while the clinician locates the fovea, and still provides sufficient illumination of the right color band to ensure a consistent bleach condition of the retinal photopigments (rhodopsin). This is important so that the reflection algorithm of the human rhodopsin matches the assumed values in the instrument software algorithm. Broadband (typically 400-880 nm) LED light is provided for measurement. This consists of the summation of a series of LEDs into a LED "engine" whose spectra are chosen and/or modified by phosphors such that the total spectra will span the range of 400 to 880 nm without a gap in coverage. The intensities of each of the LEDs in the engine may be adjusted to compensate for spectral reflectivity of the macula and the spectral transmission and responsivity of the MPR optics and spectrometer, respectively.

In addition to providing a hand-held MPR having the advantages described herein, the hand-held MPR of the present invention may be used to provide measurements of biomarkers to assist in identifying patients at risk of developing eye diseases and conditions. For example, macular pigment optical density (MPOD) is considered a biomarker for eye diseases and conditions, such as AMD, diabetic retinopathy, cataract formation and decreased visual performance. Visual performance includes contrast sensitivity, photosensitivity, dark adaptation, glare recovery, temporal processing speed, reaction time and hand/eye coordination. Functionally, improved visual performance is relevant to sports performance, aviation and driving—especially at night or in the rain.

Furthermore, recent research shows that a patient's MPOD score may be a biomarker for patients at risk of developing non eye-related diseases and conditions, including diabetes, lowered cognitive function and certain types of cancer. Thus, diagnostic use of the hand-held MPR may provide useful information to patients as an indicator of eye diseases and non-eye-related conditions. While some specific uses of the hand-held MPR are described herein, such uses are not an exhaustive listing, and additional uses of the hand-held MPR are contemplated. For example, additional characteristics of the eye may be determined using the multistep alignment process described herein, including measurement of melanin density and lens optical density, The details of analysis that determines these density values is set forth in U.S. Pat. No. 7,467,870.

Other embodiments of the present invention include a reflectometry instrument to measure macular pigment of a macula of a human eye that comprises a housing including a lower hand-held portion; a light source within the housing for emitting an illumination beam in a direction toward the macula; a spectrometer within the housing for measuring a detection beam, the detection beam being a portion of the illumination beam reflected from the macula, the detection beam being indicative of the amount of the macular pigment in the macula; and wherein the hand-held portion is graspable by the operator for assisting in manual alignment of the illumination beam with the macula.

Another embodiment of the present invention includes a hand-held reflectometry instrument to measure macular pigment of a macula of a human eye, that comprises a housing including an actuatable trigger having at least a first position and a second position; a light source within the housing for emitting an illumination beam in a direction toward the macula; a spectrometer within the housing for measuring a detection beam, the detection beam being a portion of the illumination beam reflected from the macula, the detection beam being indicative of the amount of the macular pigment in the macula; and wherein, in the first position, the actuatable trigger permits alignment of the instrument relative to the eye and, in the second position, the actuatable trigger causes the operation of the light source.

Another embodiment of the present invention includes a hand-held reflectometry instrument to measure macular pigment of a macula of a human eye, that comprises a housing including an actuatable trigger having at least a first position and a second position; a light source within the housing for emitting an illumination beam in a direction toward the macula; a spectrometer within the housing for measuring a detection beam, the detection beam being a portion of the illumination beam reflected from the macula, the detection beam being indicative of the amount of the macular pigment in the macula; and wherein, in the first position, the actuatable trigger permits alignment of the instrument relative to the eye and, in the second position, the actuatable trigger causes the operation of the light source.

Another embodiment of the invention includes a reflectometry instrument to measure macular pigment of a macula of a human eye, that comprises a housing including a lower hand-held portion; a light source within the housing for emitting an illumination beam in a direction toward the macula; a spectrometer within the housing for measuring a detection beam, the detection beam being a portion of the illumination beam reflected from the macula, the detection beam being indicative of the amount of the macular pigment in the macula; and a display on the housing that provides at least one of (i) an image of an output corresponding to the amount of the macular pigment in the macula, and (ii) an image of the eye for alignment or measurement purposes.

Another embodiment of the present invention includes a reflectometry system to measure macular pigment of a macula of a human eye, that comprises a handheld reflectometry instrument having a light source for emitting an illumination beam in a direction toward the macula, and a spectrometer within the housing for measuring a detection beam, the detection beam being a portion of the illumination beam reflected from the macula, the detection beam being indicative of the amount of the macular pigment in the macula; and a docking station for receiving the handheld reflectometry instrument.

Another embodiment of the present invention includes a method of determining the amount of macular pigment in the macula of a human eye, that comprises using a multi-step alignment process involving (i) a first light source to provide an alignment relative to the patient's pupil, and (ii) a second light source to provide alignment relative to the patient's retina after alignment relative to the patient's pupil; after the alignment process, passing an illumination beam through a lens system and onto the macula; receiving, with a spectrometer, a detection beam reflected from the macula; and measuring characteristics of the detection beam at the spectrometer.

Another embodiment of the present invention includes a method of determining the amount of macular pigment in the macula of a human eye using a handheld macular pigment measuring instrument, that comprises displaying a multi-step alignment process on a display mounted on the instrument, the displaying includes (i) a first image providing an alignment of the instrument relative to the patient's pupil, and (ii) a second image providing an alignment of the instrument relative to the patient's retina; after the alignment process, passing an illumination beam through a lens system and onto the macula; receiving, with a spectrometer, a detection beam reflected from the macula; and measuring characteristics of the detection beam at the spectrometer.

Another embodiment of the present invention includes a reflectometry instrument to measure macular pigment of a macula of a human eye, that comprises a housing including a lower hand-held portion; a light source within the housing for emitting an illumination beam in a direction toward the macula, the lights source providing a pulse of light that has a duration of less than 1 second; a spectrometer within the housing for measuring a plurality of spectra samples of a detection beam, the detection beam being a portion of the illumination beam reflected from the macula, each of the plurality of spectra samples being indicative of the amount of the macular pigment in the macula.

Each of these embodiments and obvious variations thereof is contemplated as falling within the spirit and scope of the claimed invention, which is set forth in the following claims.

What is claimed is:

1. A reflectometry instrument to measure macular pigment of a macula of a human eye, comprising:
   a housing including a lower hand-held portion;
   an assembly of optical elements arranged within the housing to sequentially image the eye with multiple fields of view and to illuminate the eye with multiple light sources;
   an actuatable trigger having a first trigger switch position, a second trigger switch position and a third trigger switch position;
   a spectrally-modifiable light source for emitting an illumination beam in a direction toward the macula, the spectrally-modifiable light source providing a range of spectra depending on the position of the actuatable trigger; and
   a spectrometer for measuring one or more spectra measurements of a detection beam, the detection beam being reflected from the macula, each of the one or more spectra measurements being indicative of the amount of the macular pigment in the macula, and combining the one or more spectra measurements to result in a macular pigment optical density measurement.

2. The reflectometry instrument according to claim 1, wherein the macular pigment optical density measurement includes lutein and zeaxanthin optical densities.

3. The reflectometry instrument according to claim 1, wherein combining the one or more spectra includes statistical averaging and filtering.

4. The reflectometry instrument according to claim 1, wherein the first trigger switch position corresponds to spectra in the range of 680-900 nm.

5. The reflectometry instrument according to claim 1, wherein the second trigger switch position corresponds to spectra in the range of 630-880 nm.

6. The reflectometry instrument according to claim 1, wherein the third trigger switch position corresponds to spectra in the range of 400-880 nm.

7. A hand-held reflectometry instrument to measure macular pigment of a macula of a human eye, comprising:
   a housing including an actuatable trigger having a first switch position, a second switch position and a third switch position;
   a first light source within the housing for emitting an illumination beam in a direction toward the macula; and
   a spectrometer within the housing for measuring a detection beam, the detection beam being a portion of the illumination beam reflected from the macula, the detection beam being indicative of the amount of the macular pigment in the macula.

8. The hand-held reflectometry instrument of claim 7, wherein a hand-held portion is graspable by an operator for assisting in manual alignment of the illumination beam with the macula.

9. The hand-held reflectometry instrument of claim 7, further comprising a light source engine, wherein in the first switch position, the actuatable trigger permits alignment of the instrument relative to an anterior portion of the eye, and in the second switch position, the actuatable trigger causes the operation of the light source engine and facilitates alignment to a posterior portion of the eye.

10. The hand-held reflectometry instrument of claim 7, further comprising a second light source for aligning the instrument, and wherein in the first switch position, the actuatable trigger activates the first light source for assisting in aligning the instrument to the eye, and in the second switch position, the actuatable trigger activates the second light source for completion of the alignment of the eye, and wherein the second light source includes a different spectral composition than the first light source.

11. The hand-held reflectometry instrument of claim 10, wherein in the third switch position, the actuatable trigger activates a measurement function of the instrument for providing that all returning light is directed down a posterior optical path to the spectrometer.

12. The hand-held reflectometry instrument of claim 7, further comprising a display on the housing that provides at least one of (i) an image of an output corresponding to the amount of the macular pigment in the macula, and (ii) an image of the eye for alignment or measurement purposes.

13. The hand-held reflectometry instrument of claim 7, further comprising a first port, the first port being connectable to a second port of a docking station for receiving the hand-held reflectometry instrument.

14. The hand-held reflectometry instrument of claim 13, wherein the first port and the second port are connectable when the instrument is docked on the docking station, the first port and the second port transmitting power to a rechargeable battery within the instrument.

15. The hand-held reflectometry instrument of claim 13, wherein the first port and the second port are connectable when the instrument is docked on the docking station, the first port and the second port transmitting data regarding the macular pigment measured by the instrument.

16. The hand-held reflectometry instrument of claim 13, wherein at least one of the instrument and docking station includes a port for communicating macular pigment data measured by the instrument to a medical data system.

17. The hand-held reflectometry instrument of claim 13, wherein at least one of the instrument and docking station includes a port for communicating macular pigment data measured by the instrument to a computer.

18. The hand-held reflectometry instrument of claim 7, wherein the instrument measures the relative amounts of zeaxanthin and lutein in the macular pigment.

19. A method of determining an amount of macular pigment in the macula of a human eye, comprising:
    using a multi-step alignment process involving (i) a first light source to provide an alignment relative to a patient's pupil, and (ii) a second light source to provide alignment relative to the patient's retina after alignment relative to the patient's pupil;
    after the alignment process, (iii) activating a measurement process by passing an illumination beam through a lens system and onto the macula;
    receiving, with a spectrometer, a detection beam reflected from the macula; and
    measuring characteristics of the detection beam at the spectrometer.

20. The method of claim 19, wherein the multi-step alignment process includes receiving multiple signals from a switch associated with a trigger on a handheld instrument, a first one of the trigger signals activating the first light source, a second one of the trigger signals activating the second light source, and a third one of the trigger signals activating the measurement process.

21. The method of claim 20, wherein the third one of the trigger signals activates the illumination beam for passing the illumination beam through the lens system and onto the macula and back to the spectrometer for multiple measurements, the multiple measurements being combined, through statistical averaging and filtering, to result in a macular pigment optical density measurement, including lutein and zeaxanthin optical densities.

22. The method of claim 19, wherein additional characteristics of the eye may be determined using the multi-step alignment process, including melanin density and lens optical density.

* * * * *

UNITED STATES PATENT AND TRADEMARK OFFICE
CERTIFICATE OF CORRECTION

PATENT NO. : 8,485,664 B2
APPLICATION NO. : 13/273050
DATED : July 16, 2013
INVENTOR(S) : T. Scott Rowe Page 1 of 1

It is certified that error appears in the above-identified patent and that said Letters Patent is hereby corrected as shown below:

In the Specification

On Column 3, Line 5, please delete the word "minor" and insert -- mirror --, therefor.
On Column 7, Line 20, please delete the word "minor" and insert -- mirror --, therefor.
On Column 7, Line 26, please delete the word "minor" and insert -- mirror --, therefor.
On Column 7, Line 29, please delete the word "minor" and insert -- mirror --, therefor.
On Column 10, Line 8, please delete the word "minor" and insert -- mirror --, therefor.
On Column 10, Line 22, please delete the word "minor" and insert -- mirror --, therefor.
On Column 10, Line 24, please delete the word "minor" and insert -- mirror --, therefor.
On Column 10, Line 42, please delete the word "minor" and insert -- mirror --, therefor.
On Column 10, Line 42, please delete the word "minor" and insert -- mirror --, therefor.
On Column 10, Line 62, please delete the word "minor" and insert -- mirror --, therefor.
On Column 12, Line 14, please delete the word "minor" and insert -- mirror --, therefor.
On Column 12, Line 47, please delete the word "minor" and insert -- mirror --, therefor.
On Column 13, Line 23, please delete the word "minor" and insert -- mirror --, therefor.
On Column 13, Line 25, please delete both instances of the word "minor" between "the" and "67" and insert -- mirror --, therefor.
On Column 13, Line 51, please delete the word "minor" and insert -- mirror --, therefor.
On Column 13, Line 52, please delete the word "minor" and insert -- mirror --, therefor.
On Column 14, Line 11, please delete the word "minor" and insert -- mirror --, therefor.
On Column 14, Line 15, please delete the word "minor" and insert -- mirror --, therefor.
On Column 15, Line 38, please delete the word "minor" and insert -- mirror --, therefor.
On Column 15, Line 39, please delete the word "minor" and insert -- mirror --, therefor.
On Column 16, Line 4, please delete the word "minor" and insert -- mirror --, therefor.
On Column 16, Line 31, please delete the word "minor" and insert -- mirror --, therefor.
On Column 17, Line 20, please delete the word "minor" and insert -- mirror --, therefor.
On Column 17, Line 22, please delete the word "minor" and insert -- mirror --, therefor.

Signed and Sealed this
Twenty-eighth Day of October, 2014

Michelle K. Lee
*Deputy Director of the United States Patent and Trademark Office*